US012605449B2

(12) United States Patent
Kim et al.

(10) Patent No.: US 12,605,449 B2
(45) Date of Patent: Apr. 21, 2026

(54) DRUG-CLAY MINERAL COMPLEX CONTAINING PHOSPHOLIPID AND ORAL ADMINISTRATION COMPOSITION INCLUDING SAME

(71) Applicant: Korea Institute of Geoscience and Mineral Resources, Daejeon (KR)

(72) Inventors: Jae Hwan Kim, Gyeongsangbuk-do (KR); Il Mo Kang, Seoul (KR); Dae Duk Kim, Seoul (KR); Jang Ik Lee, Seoul (KR); Gyu Ho Kim, Seoul (KR); Min Jun Baek, Seoul (KR); Chang Yun Park, Seoul (KR); Ki Min Roh, Daejeon (KR); Sung Man Seo, Gyeongsangbuk-do (KR)

(73) Assignee: Korea Institute of Geoscience and Mineral Resources, Daejeon (KR)

( * ) Notice: Subject to any disclaimer, the term of this patent is extended or adjusted under 35 U.S.C. 154(b) by 587 days.

(21) Appl. No.: 18/013,919

(22) PCT Filed: Jul. 1, 2021

(86) PCT No.: PCT/KR2021/008317

§ 371 (c)(1),
(2) Date: Dec. 30, 2022

(87) PCT Pub. No.: WO2022/005216

PCT Pub. Date: Jan. 6, 2022

(65) Prior Publication Data

US 2023/0321249 A1 Oct. 12, 2023

(30) Foreign Application Priority Data

Jul. 1, 2020 (KR) ........................ 10-2020-0080930

(51) Int. Cl.
*A61K 47/52* (2017.01)
*A61K 47/54* (2017.01)

(52) U.S. Cl.
CPC ............ *A61K 47/52* (2017.08); *A61K 47/544* (2017.08)

(58) Field of Classification Search
None
See application file for complete search history.

(56) References Cited

U.S. PATENT DOCUMENTS

2002/0047058 A1* 4/2002 Verhoff .................... A61K 9/14 241/26

FOREIGN PATENT DOCUMENTS

| | | |
|---|---|---|
| JP | 02-267114 | 10/1990 |
| JP | 2007-308380 | 11/2007 |
| KR | 10-2008-0080973 | 9/2008 |
| KR | 10-2054346 | 12/2009 |
| KR | 10-2019-0086344 | 7/2019 |
| KR | 10-2212402 | 2/2021 |
| WO | WO 2008/063910 | 5/2008 |
| WO | WO 2019/138398 | 7/2019 |

OTHER PUBLICATIONS

Meng et al. "Preparation and Characterization of Lecithin-Heparin Intercalated in Montmorillonite Nanocomposite", Applied Clay Science, 162: 454-460, Available Online Jul. 4, 2018.
Quellet-Plamondon et al. "The Effect of Cationic, Non-Ionic and Amphiphilic Surfactants on the Intercalation of Bentonite", Colloids and Surfaces A: Physicochemical and Engineering Aspects, 444: 330-337, Available Online Dec. 24, 2013.
Wicklein et al. "Bio-Organoclays Based on Phospholipids as Immobilization Hosts for Biological Species", Langmuir, 26(7): 5217-5225, Published on Web Jan. 25, 2010.
International Search Report and the Written Opinion Dated Sep. 27, 2021 From the International Searching Authority Re. Application No. PCT/KR2021/008317 and its Translation into English. (11 Pages).
Baek et al. "Preparation and Evaluation of the Doxazosin-Bentonite Composite as A PH-Dependent Controlled-Release Oral Formulation", Applied Clay Science, 229: 106677-1-106677-9, Nov. 1, 2022.
Baek et al. "Preparation and Evaluation of the Doxazosin-Bentonite Composite as A PH-Dependent Controlled-Release Oral Formulation", Applied Clay Science, Table S1, Nov. 1, 2022.
Liu et al. "Multifunctional Silica Nanoparticles for Targeted Delivery of Hydrophobic Imaging and Therapeutic Agents", International Journal of Pharmaceutics, 421(2): 370-378, Available Online Oct. 6, 2011.
Liu et al. "Preparation and Characterization of Organo-Vermiculite Based on Phosphatidylcholine and Adsorption of Two Typical Antibiotics", Applied Clay Science, 137: 160-167, Available Online Dec. 22, 2016.
Yang et al. "Aminoclay-Lipid Hybrid Composite as a Novel Drug Carrier of Fenofibrate for the Enhancement of Drug Release and Oral Absorption", International Journal of Nanomedicine, 11: 1067-1076, Published Online Mar. 15, 2016.

* cited by examiner

*Primary Examiner* — Aradhana Sasan

(57) ABSTRACT

According to one embodiment of the present invention, provided is a drug-clay mineral complex, in which the complex comprises a phospholipid, and the drug has an amine group.

9 Claims, 21 Drawing Sheets

DRUG-CLAY MINERAL COMPLEX CONTAINING PHOSPHOLIPID AND ORAL ADMINISTRATION COMPOSITION INCLUDING SAME

RELATED APPLICATIONS

This application is a National Phase of PCT Patent Application No. PCT/KR2021/008317 having International filing date of Jul. 1, 2021, which claims the benefit of priority of Korean Patent Application No. 10-2020-0080930 filed on Jul. 1, 2020. The contents of the above applications are all incorporated by reference as if fully set forth herein in their entirety.

FIELD AND BACKGROUND OF THE INVENTION

The following description relates to a drug-clay mineral complex, a complex containing a phospholipid, an oral administration composition including the same, and a preparation method of a drug-clay mineral complex.

In order for an orally administered drug to have a sufficient pharmacological effect, a drug needs to be properly absorbed throughout the body through the gastrointestinal tract to exhibit high bioavailability and efficacy. In order for a drug to be absorbed, the drug needs to be sufficiently dissolved and released in the gastrointestinal tract, and the released drug molecules need to penetrate an intestinal membrane. However, poorly soluble drugs with low solubility are not sufficiently released in the gastrointestinal tract, resulting in low bioavailability.

Therefore, in order to improve the absorption of these poorly soluble drugs, it is very important to improve solubility and release characteristics in the gastrointestinal tract. Since sorafenib itself has high gastrointestinal permeability, it is possible to achieve sufficient absorption improvement and high bioavailability just by improving solubility and release characteristics, and in addition, since a target effective blood concentration may be reached more quickly, the reduction of a treatment period can also be expected.

Conventionally, in order to improve the absorption of poorly soluble drugs, there has been proposed a method of applying a drug in a dissolved state using a co-solvent, an emulsion, etc., but since these methods require the use of large amount of organic solvents, surfactants, and so forth, required to dissolve poorly soluble drugs, toxicity to the gastrointestinal tract, side effects, and so forth, may be problematic. In addition, when the co-solvent, the emulsion, etc. are diluted in the gastrointestinal tract, recrystallization and precipitation of poorly soluble drugs due to a decrease in solubility may occur, and thus, there may be a problem that it is difficult to be released again.

In order to solve this problem, an oral administration composition with controlled release was developed by developing a complex of a conventional clay mineral and a compound having a medicinal effect (Korean Patent Registration No. 10-2054346), but there is a disadvantage in that the release rate of the compound is low.

SUMMARY OF THE INVENTION

Under this background, the present inventors have found that when a phospholipid such as phosphatidylcholine was introduced into a clay mineral, the release amount of the drug in the intestine was increased while the controlled release of the drug was maintained, ultimately improving the oral bioavailability, and then completed the present disclosure.

Accordingly, an aspect provides a drug-clay mineral complex containing a phospholipid and an oral administration composition containing the same.

Another aspect provides a preparation method of a drug-clay mineral complex including the phospholipid.

According to an aspect, there is provided a drug-clay mineral complex, in which the complex contains a phospholipid, and the drug has an amine group.

According to an aspect, the drug may be at least one selected from the group consisting of quetiapine, ciprofloxacin, docetaxel, camptothecin, carbamazepine, prazosin, doxazosin, olanzapine, ziprasidone, aripiprazole, and risperidone.

According to an aspect, the drug may be present in an amorphous state in a layered structure of the clay mineral.

According to an aspect, the phospholipid may be at least one selected from the group consisting of phosphatidylcholine, phosphatidylserine, phosphatidylethanolamine, phosphatidylglycerol and phosphatidylinositol.

According to an aspect, the clay mineral may be at least one selected from the group consisting of bentonite, smectite, vermiculite, beidellite, nontronite, saponite and hectorite.

According to an aspect, the drug-clay mineral complex of the present disclosure may include 2 to 30 wt % of the phospholipid and 1 to 50 wt % of the drug.

According to an aspect, a maximum drug release rate in a release solution at pH 7.4 may be increased by 1.5 times greater than a drug-clay mineral complex having the same composition except that the phospholipids is not included.

According to an aspect, the maximum drug release rate in the release solution at pH 7.4 may be 80% or more of the drug content.

According to another aspect, there is provided an oral administration composition including the drug-clay mineral complex.

According to yet another aspect, there is provided a preparation method of a drug-clay mineral complex including: preparing a phospholipid-clay mineral complex by mixing a phospholipid aqueous solution prepared by dissolving a phospholipid in an organic solvent and a hydrophilic solvent and a clay mineral suspension; preparing an aqueous drug solution by dissolving a drug compound having an amine group in a hydrophilic solvent; and mixing the aqueous drug solution and a suspension of the phospholipid-clay mineral complex.

According to an aspect, the drug compound having the amine group may be at least one selected from the group consisting of quetiapine, ciprofloxacin, docetaxel, camptothecin, carbamazepine, prazosin, doxazosin, olanzapine, ziprasidone, aripiprazole, and risperidone.

According to an aspect, the phospholipid may be at least one selected from the group consisting of phosphatidylcholine, phosphatidylserine, phosphatidylethanolamine, phosphatidylglycerol and phosphatidylinositol.

According to an aspect, the clay mineral may be at least one selected from the group consisting of bentonite, smectite, vermiculite, beidellite, nontronite, saponite and hectorite.

According to an aspect, the organic solvent may be at least one selected from the group consisting of methanol, ethanol, propanol, acetone, acetonitrile, butanediol, diethanolamine, formamide, dimethylformamide, dimethylsulfoxide, dimethylacetamide, glycerol, tetrahydrofuran, and propylene glycol.

According to an aspect, the hydrophilic solvent may be an acidic aqueous solution having a pH of 5 or less.

According to an aspect, the acidic aqueous solution may contain at least one selected from the group consisting of hydrochloric acid, phosphoric acid, sulfuric acid, acetic acid, and formic acid.

According to the present disclosure, the drug-clay mineral complex contains the phospholipids to have a solubilization effect of the phospholipid, thereby improving the low drug release rate and bioavailability of a conventional drug-clay mineral complex without containing a phospholipid.

DESCRIPTION OF SPECIFIC EMBODIMENTS OF THE INVENTION

Figure 1:
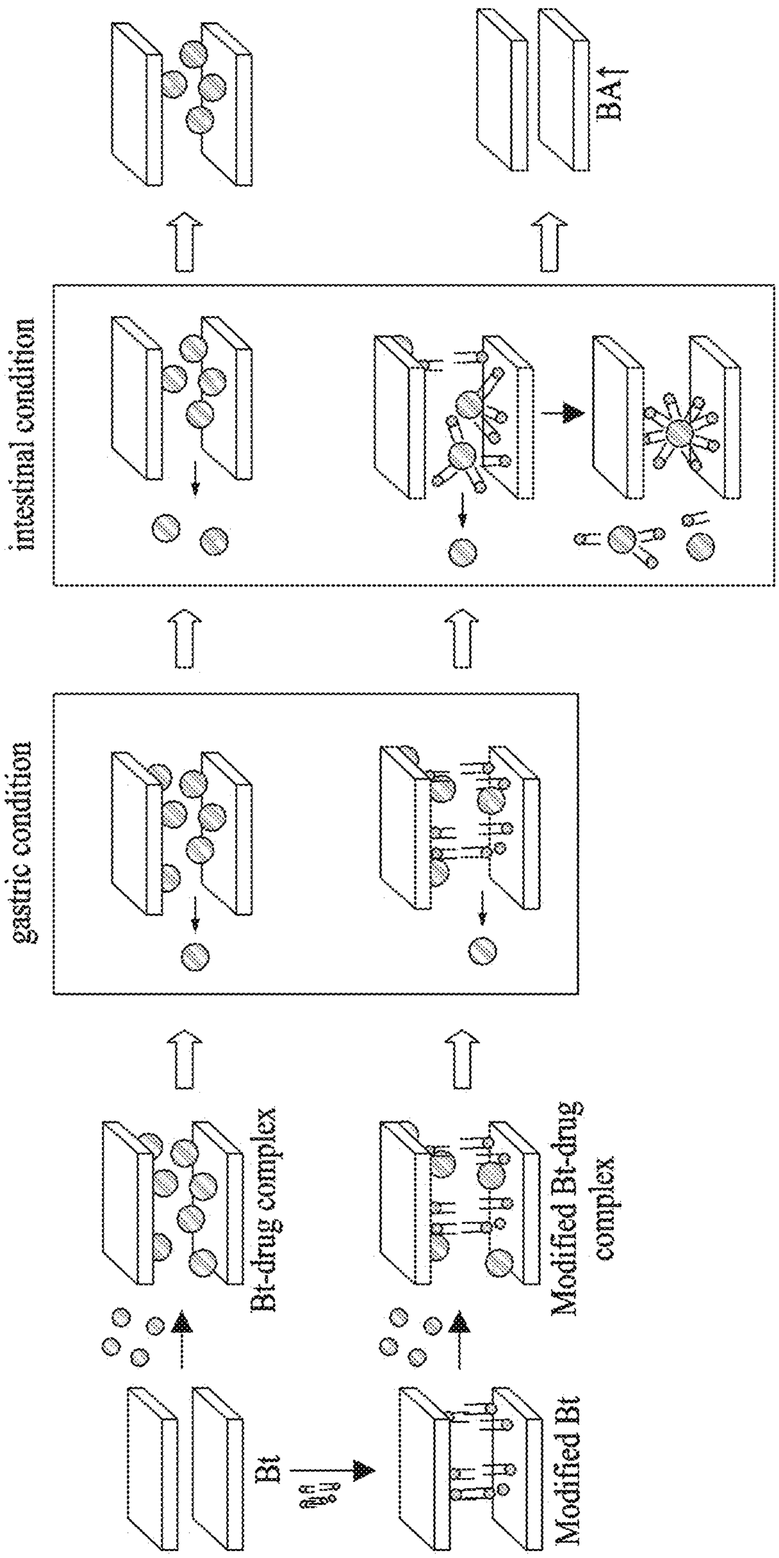
FIG. 1 is a diagram illustrating structures of a drug-clay mineral complex containing phospholipid and a phospholipid-clay mineral complex, and a drug release behavior in the gastric and intestinal environments according to an example embodiment.

Hereinafter, example embodiments will be described in detail with reference to the accompanying drawings. However, since various modifications may be made to the example embodiments, the scope of the present disclosure is not limited or restricted by these example embodiments. It should be understood that all modifications, equivalents and substitutes for the example embodiments are included in the scope of the present disclosure.

The terms used in the example embodiments are used for the purpose of description only and should not be construed to be limited. The singular expression includes the plural expression unless the context clearly dictates otherwise. In the present application, it should be understood that term "comprising" or "having" indicates that a feature, a number, a step, an operation, a component, a part or the combination thereof described in the specification is present but does not exclude a possibility of presence or addition of one or more other features, numbers, steps, operations, components, parts or combinations thereof, in advance.

Unless otherwise contrarily defined, all terms used herein including technological or scientific terms have the same meanings as those generally understood by a person with ordinary skill in the art to which example embodiments pertain. Terms which are defined in a generally used dictionary should be interpreted to have the same meaning as the meaning in the context of the related art and are not interpreted as ideal or excessively formal meanings unless otherwise defined in the present application.

In addition, in the description with reference to the accompanying drawings, like components designate like reference numerals regardless of reference numerals and a duplicated description thereof will be omitted. In describing the example embodiments, a detailed description of related known technologies will be omitted if it is determined that they unnecessarily make the gist of the example embodiments unclear.

In describing the components of the example embodiments of the present disclosure, terms including first, second, A, B, (a), (b), and the like may be used. These terms are just intended to distinguish the components from other components, and the terms do not limit the nature, sequence, or order of the components.

Components included in any one example embodiment and components having a common function will be described using the same names in other example embodiments. Unless otherwise stated, descriptions described in any one example embodiment may also be applied to other example embodiments, and detailed descriptions in the overlapping range will be omitted.

According to one example embodiment of the present disclosure, there is provided a drug-clay mineral complex, in which the complex contains a phospholipid, and the drug has an amine group.

The drug may be at least one selected from the group consisting of quetiapine, ciprofloxacin, docetaxel, camptothecin, carbamazepine, prazosin, doxazosin, olanzapine, ziprasidone, aripiprazole, and risperidone.

The quetiapine is 2-[2-(4-dibenzo[b,f][1,4]thiazepin-11-yl-1-piperazinyl) ethoxy]-ethanol fumarate, a compound having a structure represented by Chemical Formula 1 below.

The quetiapine is used to relieve symptoms of bipolar disorder and depression.

[Chemical Formula 1]

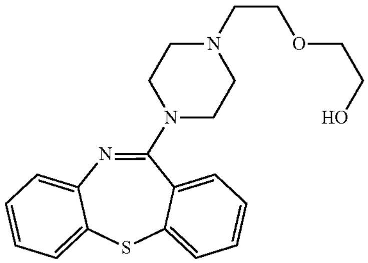

Ciprofloxacin is 1-cyclopropyl-6-fluoro-1,4-dihydro-4-oxo-7-(1-piperazinyl)-quinoline-3-carboxylic acid, a compound having a structure of Chemical Formula 2 below.

[Chemical Formula 2]

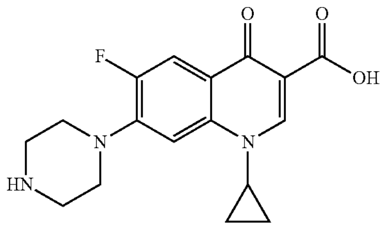

Camptothecin is(S)-4-ethyl-4-hydroxy-1H-pyrano-[3',4':6,7]indolizinol[1,2-b]quinoline-3,14 (4H, 12H)-dione, a compound having a structure of Chemical Formula 3 below.

[Chemical Formula 3]

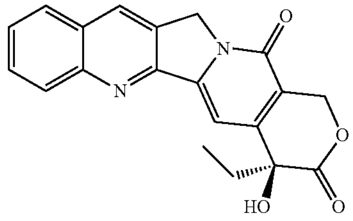

Carbamazepine is 5H-dibenzo[b,f]azepine-5-carboxamide, a compound having a structure of Chemical Formula 4 below.

[Chemical Formula 4]

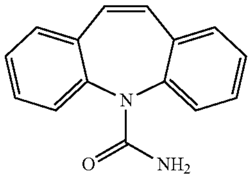

Prazosin is 4-amino-6,7-dimethoxy2-[4-(furo-2-yl)-piperazin-1-yl]-quinazoline, a compound having a structure of Chemical Formula 5 below.

[Chemical Formula 5]

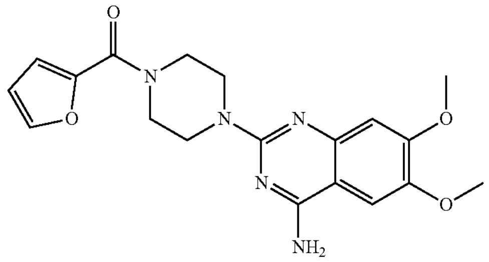

Doxazosin is (RS)-2-[4-(2,3-dihydro-1,4-benzodioxin-2-carbonyl) piperazin-1-yl]-6,7-dimethoxyquinazoline-4-amine, a compound having a structure of Chemical Formula 6 below.

[Chemical Formula 6]

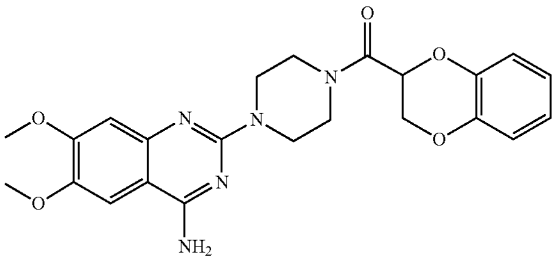

Olanzapine is 2-methyl-4-(4-methyl-1-piperazinyl)-10H-thieno[2,3-b][1,5]benzodiazepine, a compound having a structure of Chemical Formula 7 below.

[Chemical Formula 7]

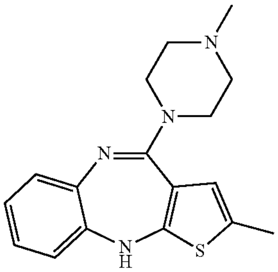

Ziprasidone is (5-[2-[4-(1,2-benzisothiazol-3-yl)-1-piperazinyl]ethyl]-6-chloro-1,3-dihydro-2H-indol-2-one), a compound having a structure of Chemical Formula 8 below.

[Chemical Formula 8]

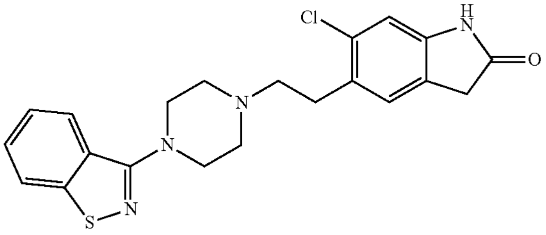

Aripiprazole is 7-{4-[4-(2,3-dichlorophenyl) piperazin-1-yl]butoxy}-3,4-dihydroquinolin-2 (1H)-one, a compound having a structure of Chemical Formula 9 below.

[Chemical Formula 9]

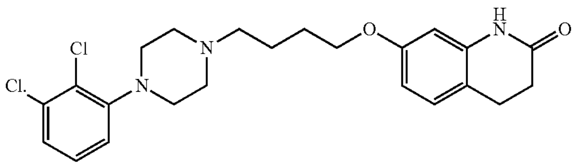

Risperidone is (3-[2-[4-(6-fluoro-1,2-benzisoxazol-3-yl) piperidinyl]ethyl-6,7,8,9-tetrahydro-2-methyl-4H-pyrido-[1,2]pyrimidin-4-one, a compound having a structure of Chemical Formula 10 below.

[Chemical Formula 10]

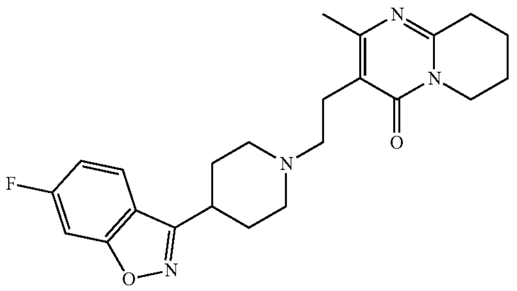

These drugs are compounds having amine groups, and a common physicochemical characteristic thereof is that the pKa values are approximately in a range of 2 to 7. In this case, since the drugs have cationic properties in an acidic environment of low pH, the drugs may have high solubility (20 mg/mL or more at pH 1), and at pH 7 or more, the drugs become a neutral compound and are easily released from the intestinal environment. In addition, the cationic compound has an advantage of binding to or being adsorbed on a layered structure of the clay mineral. Specifically, the drugs having the amine groups are bound or adsorbed between anionic crystal units of the clay mineral to form a complex with the clay mineral (see FIG. 1), and the drugs are present in an amorphous state in the layered structure of the clay mineral.

The phospholipid contained in the complex of the present disclosure may exist in a state of being ionically bound to or physically adsorbed to the clay mineral. For example, the phospholipids is bound or adsorbed to the surface of the clay mineral or between anionic crystal units of the clay mineral in the form of cations, resulting in existing in the form of being bound between plate structures of the clay mineral (see FIG. 1). On the other hand, when the phospholipid bound to the clay mineral reaches the intestinal environment of pH 7 or higher, a phosphate group portion becomes negatively charged to become electrically neutral, and as a result, the ionic interaction with the clay mineral is weakened and the phospholipid may be released from the clay mineral.

In the present disclosure, the phospholipid is amphiphilic and also acts as a surfactant in vivo. Examples of the phospholipid may be at least one selected from the group consisting of phosphatidylcholine, phosphatidylserine, phosphatidylethanolamine, phosphatidylglycerol and phosphatidylinositol, but are not limited thereto, and as a lipid surfactant, phytosphingosine, sphinganine, sphingosine, and so forth corresponding to vegetable phospholipids may be further used.

In the present disclosure, the clay mineral has a plate-like structure having interlayer expansibility due to lack of hydrogen bond between crystal units and may be used as a clay mineral that may be used as a carrier by inserting a drug therein. Meanwhile, in the clay mineral having interlayer expansibility, tetrahedral Si having a tetravalent positive charge is isomorphic-substituted to Al or Fe having a trivalent positive charge or octahedral Al or $Fe^{3+}$ having a trivalent positive charge is isomorphic-substituted to Mg or $Fe^{2+}$ having a bivalent positive charge to generate a negative layer charge, but cations such as calcium ions ($Ca^{2+}$), magnesium ions ($Mg^{2+}$), sodium ions ($Na^{+}$), potassium ions ($K^{+}$), and so forth are bound between the layers or on the surface to have overall electrical neutrality. Therefore, the clay mineral has excellent adsorption/binding ability to cationic substances.

The clay mineral used in the present disclosure may be a smectite-based mineral, and may be, for example, one or more selected from the group consisting of bentonite, illite, beidellite, hectorite, glauconite, nontronite, and saponite. Preferably, bentonite containing 50 wt % or more of montmorillonite may be used.

Since the adsorption/binding ability of the clay mineral to the cationic drug varies depending on the pH of the surrounding environment, the drug-clay mineral complex of the present disclosure may continuously release the drug bound to the clay mineral at a low release rate while moving from the upper digestive tract to the lower digestive tract. Therefore, the complex of the present disclosure may contribute to maintaining a relatively constant blood drug concentration as a drug carrier that controls the drug release. In addition, when the drug-clay mineral complex contains the phospholipid, the phospholipid of which an electrical state is changed may be released together with the drug while the complex passes through the small intestine. That is, since the phospholipid released from the complex acts as a solubilizer and helps to sufficiently release the drug bound to the clay mineral, the complex of the present disclosure may improve the release rate of the drug while maintaining the controlled release which is a characteristic of the clay mineral, thereby ultimately improving the bioavailability.

Here, the modified- or controlled-release means that the blood concentration of the drug after administration of the drug is rapidly increased to an effective concentration, the blood drug concentration is constantly maintained only for a desired time, so that an administration frequency is lower than those of general other preparations, a bioreaction is uniform, and side effects are small.

The drug-clay mineral complex of the present disclosure may include the phospholipid of 2 to 30 wt %, preferably 5 to 20 wt % and the drug of 1 to 50 wt %, preferably 3 to 30 wt %. When an excessive amount of phospholipid or drug reacts with the clay mineral, it is not preferable because the phospholipid or drug is not bound to the clay mineral and a lost ratio is increased, and when the phospholipid is excessively contained, there is a problem in that the drug loading amount of the complex is reduced.

The drug-clay mineral complex of the present disclosure has a maximum drug release rate in a release solution at pH 7.4 which may be increased by 1.5 times greater than a drug-clay mineral complex having the same composition except that the phospholipid is not included, which is because the phospholipid released in a lower digestive tract environment acts as a solubilizer to induce the release of the drug. Accordingly, the drug-clay mineral complex of the present disclosure exhibits a very high maximum drug release rate in a release solution of a pH of 7.4 as 80% or more of the drug content.

According to another example embodiment of the present disclosure, there is provided an oral administration composition including a drug-clay mineral complex including the phospholipid. When the composition is administered orally, the drug is stably delivered through the upper digestive tract to the lower digestive tract while being adsorbed to the clay mineral, so that the drug release is delayed, and the drug is continuously released and absorbed due to the solubilizer effect of the phospholipid. In addition, the drug release property is controlled to prevent rapid absorption of the drug immediately after administration of the composition, and since the drug itself is well dispersed in water, there is an advantage that absorption thereof is easier than tablets.

On the other hand, the drug-clay mineral complex containing phospholipid included in the oral administration composition of the present disclosure is uniformly maintained in the blood drug concentration compared to when the drug powder is orally administered, thereby improving half-life in the calculated pharmacokinetic. The drug-clay mineral complex containing the phospholipid is uniformly maintained in a high blood drug concentration even compared to the drug-clay mineral complex without containing the phospholipids, so that it is easier to reach a drug therapeutic coefficient. Furthermore, the complex exhibits 3.8 times or higher oral bioavailability than the drug-clay mineral complex without containing the phospholipids. Therefore, the complex may be used as a more effective composition for oral administration in terms of a formulation.

The oral administration composition of the present disclosure may contain 0.01 to 80 wt %, preferably 0.02 to 65 wt % of the drug-clay mineral complex containing the phospholipid. However, the amount thereof may be increased or decreased according to the needs of a user and may be appropriately increased or decreased depending on a situation, such as age, diet, nutrition condition, and disease progression.

The oral administration composition of the present disclosure may be used in the form of a general pharmaceutical preparation. For example, the composition of the present disclosure may be used in the form of preparations for oral administration, such as tablets, granules, capsules, suspensions, and so forth, and these preparations may be prepared by using acceptable general carriers, for example, in the case of orally administered preparations, excipients, binders, disintegrants, lubricants, solubilizers, coloring agents, coating agents, suspensions, preservatives, or extenders.

The dose of the oral administration composition of the present disclosure may be determined by experts according to various factors such as the condition, age, sex, and complications of patients, but may be generally administered in a dose of 0.1 mg to 10 g per 1 kg of adult. Alternatively, the pharmaceutical composition per unit formulation is contained in a daily dose or ½, ⅓, or ¼ dose thereof, and may be administered 1 to 6 times a day, but is not limited thereto, and may be appropriately controlled by doctors in charge.

In addition, the oral administration composition of the present disclosure may further include additives in addition to the complex. The complex of the present disclosure may also be mixed directly with the additives or may be mixed with the additives in the form encapsulated in soft capsules, for example, a tablet form. When the complex powder is encapsulated in hard capsules, in order to help in release and disintegration of the compound having the efficacy, at least one selected from disintegrants, excipients, sustained release agents, lubricants, and so forth may be added in the hard capsules.

The additives may improve the physical properties of the complex powder in vivo and control the release rate of the compound and so forth. For example, the additives may include one or more selected from polyethylene glycol, polyvinylpyrrolidone, polyoxyethylene sorbitan monooleate (product name: tween-80), poloxamer, poly-oxyethylene esters of 12-hydroxystearic acid (Solutol HS15), carbomer, sodium taurocholate, and the like. In addition, the additives may further include hydroxypropylmethylcellulose, Eudragit, lactose, and so forth in order to further enhance the drug sustained-release ability of the complex. The additives may be included by approximately 0.5 to 30 wt % based on the total weight of the composition but is not limited thereto.

According to yet another example embodiment of the present disclosure, there is provided a preparation method of a drug-clay mineral complex including: preparing a phospholipid-clay mineral complex by mixing a phospholipid aqueous solution prepared by dissolving a phospholipid in an organic solvent and a hydrophilic solvent and a clay mineral suspension; preparing an aqueous drug solution by dissolving a drug compound having an amine group in a hydrophilic solvent; and mixing the aqueous drug solution and a suspension of the phospholipid-clay mineral complex.

In order to adsorb the drug to the clay mineral in an amorphous state, a method of dissolving, dispersing and mixing the drug and the clay mineral in the same aqueous solution may be used.

In the mixing of the phospholipid aqueous solution and the clay mineral suspension and the mixing of the drug aqueous solution and the suspension of the phospholipid-clay mineral complex, since some of the phospholipid or drug may exist in a dissolved state in the solvent without being adsorbed to the clay mineral, a method of precipitating the complex by centrifuging the mixed solution may be used. In addition, the complex remaining after removing a supernatant may be freeze-dried and then used.

The organic solvent may use at least one selected from the group consisting of methanol, ethanol, propanol, acetone, acetonitrile, butanediol, diethanolamine, formamide, dimethylformamide, dimethylsulfoxide, dimethylacetamide, glycerol, tetrahydrofuran and propylene glycol.

In addition, the hydrophilic solvent may be an acidic aqueous solution having a pH of 5 or less, and the acidic aqueous solution may include at least one selected from the group consisting of hydrochloric acid, phosphoric acid, sulfuric acid, acetic acid, and formic acid.

A more detailed description will be described below through the following Example Embodiments.

Materials and Methods

Bentonite was provided and used by the Korea Institute of Geoscience and Mineral Resources. Quetiapine was purchased from Tokyo Chemical Industry (TCI) and used. An experimental animal used in Experimental Example 7 was a Sprague Dawley rat (SD rat). 8-week-old SD rats were purchased from ORIENT BIO Inc. and experimented in an experimental animal room at the first basement, 143, College of Medicine of Seoul National University. The breeding conditions of the experimental animal were as follows. Temperature and humidity range of 22±2° C. and 50±5% (RH), ventilation frequency of 10 to 15 times/hour, lighting time and illumination 12 hours lighting on (lighting: 08:00 to 20:00), and illumination: 150 to 300 Lux.

Example Embodiment 1. Preparation of Drug-Clay Mineral Complex

Example Embodiment 1-1

An aqueous drug solution was prepared by dissolving 5 mg of a quetiapine compound in a 0.1 N aqueous hydrochloric acid solution at room temperature. A bentonite suspension was prepared by suspending bentonite powder in an amount corresponding to 8 times the mass of the quetiapine compound in distilled water.

Next, the aqueous drug solution and the bentonite suspension were mixed and stirred for 10 minutes to prepare a quetiapine-bentonite complex. At this time, a method of adding the bentonite suspension to the aqueous drug solution under continuous stirring was used to prevent the bentonite powder from precipitating. The solution containing the quetiapine-bentonite complex was centrifuged at 4,000 rpm for 10 minutes to precipitate the quetiapine-bentonite complex, and the supernatant was removed, and then the remaining pellet was rapidly cooled using liquid nitrogen and lyophilized to evaporate all remaining solvent.

Example Embodiment 1-2

In the same manner as described in Example Embodiment 1-1 except that the bentonite dispersion was prepared using bentonite powder of 4 times the mass of the quetiapine compound, a quetiapine-bentonite complex was prepared in a weight ratio of quetiapine and bentonite of 2:8 (using 10 mg of quetiapine and 40 mg of bentonite).

Example Embodiment 1-3

In the same manner as described in Example Embodiment 1-1 except that the bentonite dispersion was prepared using bentonite powder of 2 times the mass of the quetiapine compound, a quetiapine-bentonite complex was prepared in a weight ratio of quetiapine and bentonite of 4:8 (using 20 mg of quetiapine and 40 mg of bentonite).

Example Embodiment 1-4

In the same manner as described in Example Embodiment 1-1 except that the bentonite dispersion was prepared using bentonite powder of 1.3 times the mass of the quetiapine compound, a quetiapine-bentonite complex was prepared in a weight ratio of quetiapine and bentonite of 6:8 (using 30 mg of quetiapine and 40 mg of bentonite).

Comparative Example 1

To prepare a physical mixture of quetiapine and bentonite, a quetiapine compound and bentonite powder were added in a test tube and mixed for 30 minutes using a vortexer. The quetiapine and the bentonite were mixed in a weight ratio of 1:2 in consideration of a drug content per unit weight of the composition (quetiapine-bentonite complex in a weight ratio of 4:8) determined through optimization.

Experimental Example 1. Drug Content Per Unit Weight of Complex

For the quetiapine-bentonite complexes prepared in Example Embodiments 1-1 to 1-4, the drug content per unit weight of the complex was confirmed. To confirm the drug content, the complex was suspended in distilled water, and then the complex suspension was diluted 10-fold using phosphate buffered saline (pH 7.4) containing 1% (v/v) Tween20. The drug was extracted from the diluted dispersion using a vortexer, and the content of the drug extracted with an extraction solvent was analyzed using High Performance Liquid Chromatography (HPLC).

TABLE 1

| Example Embodiment | Weight ratio of drug:bentonite | Drug content (%) per unit weight |
|---|---|---|
| 1-1 | 1:8 | 12.81 ± 0.03 |
| 1-2 | 2:8 | 16.48 ± 0.48 |
| 1-3 | 4:8 | 19.21 ± 0.44 |
| 1-4 | 6:8 | 19.5 ± 0.92 |

As a result, it was confirmed that the drug content per unit weight of the complex was high when the weight ratio of the drug to the bentonite was 4:8. On the other hand, the drug content per unit weight was similar to that of the weight ratio of the drug to the bentonite of 6:8, but the weight ratio of 4:8 was determined as an optimal ratio in consideration of drug loss.

Example Embodiment 2. Preparation of Drug-Clay Mineral Complex Containing Phospholipid

Example Embodiment 2-1

5 mg of phosphatidylcholine was dissolved in a solvent mixed with ethanol and a 0.1 N aqueous hydrochloric acid solution. A bentonite suspension was prepared by suspending bentonite powder of 8 times the mass of the phospholipid in a solvent in which a 0.1 N aqueous hydrochloric acid solution and distilled water were mixed. Next, the phosphatidylcholine solution and the bentonite suspension were mixed and stirred for about 4 hours to prepare a phosphatidylcholine-bentonite complex. At this time, a method of adding the bentonite suspension to the phosphatidylcholine solution under continuous stirring was used to prevent the bentonite powder from precipitating. Thereafter, the phosphatidylcholine-bentonite complex was centrifuged at 4,000 rpm for 10 minutes to be precipitated to remove a supernatant and the remaining pellets were rapidly cooled using liquid nitrogen and then lyophilized to evaporate the remaining solvent.

An aqueous drug solution was prepared by dissolving a quetiapine compound corresponding to 0.5 times the mass of the phosphatidylcholine-bentonite complex powder in a 0.1 N aqueous hydrochloric acid solution at room temperature, and the lyophilized phosphatidylcholine-bentonite complex powder was suspended in distilled water to prepare a suspension of the complex. The prepared aqueous drug solution and the suspension of the complex were stirred for 10 minutes to prepare a phosphatidylcholine-quetiapine-bentonite complex in a weight ratio of phosphatidylcholine, quetiapine, and bentonite of 1:4:8.

Example Embodiment 2-2

In the same manner as in Example Embodiment 2-1, except that the bentonite dispersion was prepared using bentonite powder of 4 times the mass of phosphatidylcholine, a phosphatidylcholine-quetiapine-bentonite complex was prepared in a weight ratio of phosphatidylcholine, quetiapine, and bentonite of 2:4:8 (10 mg phosphatidylcholine+20 mg quetiapine+40 mg bentonite).

Example Embodiment 2-3

In the same manner as in Example Embodiment 2-1, except that the bentonite dispersion was prepared using bentonite powder of 2 times the mass of phosphatidylcholine, a phosphatidylcholine-quetiapine-bentonite complex was prepared in a weight ratio of phosphatidylcholine, quetiapine, and bentonite of 4:4:8 (20 mg phosphatidylcholine+20 mg quetiapine+40 mg bentonite).

Example Embodiment 2-4

In the same manner as in Example Embodiment 2-1, except that the bentonite dispersion was prepared using bentonite powder of 1.3 times the mass of phosphatidylcholine, a phosphatidylcholine-quetiapine-bentonite complex was prepared in a weight ratio of phosphatidylcholine, quetiapine, and bentonite of 6:4:8 (30 mg phosphatidylcholine+20 mg quetiapine+40 mg bentonite).

Comparative Example 2

A physical mixture of phosphatidylcholine and bentonite was prepared by setting a weight ratio of phosphatidylcholine and bentonite to 1:6, putting phosphatidylcholine and bentonite powder in a test tube, and mixing the mixture for 30 minutes using a vortexer.

Comparative Example 3

A physical mixture of quetiapine and a phosphatidylcholine-bentonite complex was prepared by setting a weight ratio of quetiapine and the phosphatidylcholine-bentonite complex to 1:9, putting quetiapine and phosphatidylcholine-bentonite powder in a test tube, and mixing the mixture for 30 minutes using a vortexer.

Experimental Example 2. Phospholipid Content Per Unit Weight of Phospholipid-Drug-Bentonite Complex For the phospholipid-drug-bentonite complexes prepared in Example Embodiments 2-1 to 2-4, a phospholipid content per unit weight of the complex was confirmed. In order to measure the phospholipid content, the phospholipid-drug-bentonite complex was suspended in distilled water, and a suspension of the complex was diluted 10-fold using a 50:50 (v/v) solution of phosphate buffered saline (pH 7.4) containing 1% (v/v) Tween20 and tetrahydrofuran. The phospholipid was extracted from the diluted dispersion using a vortexer, and the phospholipid content extracted in the extraction solvent was analyzed by liquid chromatography-mass spectrometry (LC-MS/MS).

For the phospholipid-drug-bentonite complexes prepared in Example Embodiments 2-1 to 2-4, a drug content per unit weight of the complex was confirmed. The drug content was confirmed by extracting the drug in the same manner as described in Experimental Example 1 above.

TABLE 2

| Example Embodiment | Weight ratio of phospholipid: drug:bentonite | Phospholipid content (%) per unit weight | Drug content (%) per unit weight |
|---|---|---|---|
| 2-1 | 1:4:8 | 1.37 ± 0.06 | 15.32 ± 1.80 |
| 2-2 | 2:4:8 | 3.81 ± 0.29 | 14.18 ± 0.64 |
| 2-3 | 4:4:8 | 15.58 ± 0.22 | 9.51 ± 1.28 |
| 2-4 | 6:4:8 | 20.22 ± 1.00 | 7.63 ± 0.52 |

Figure 2:
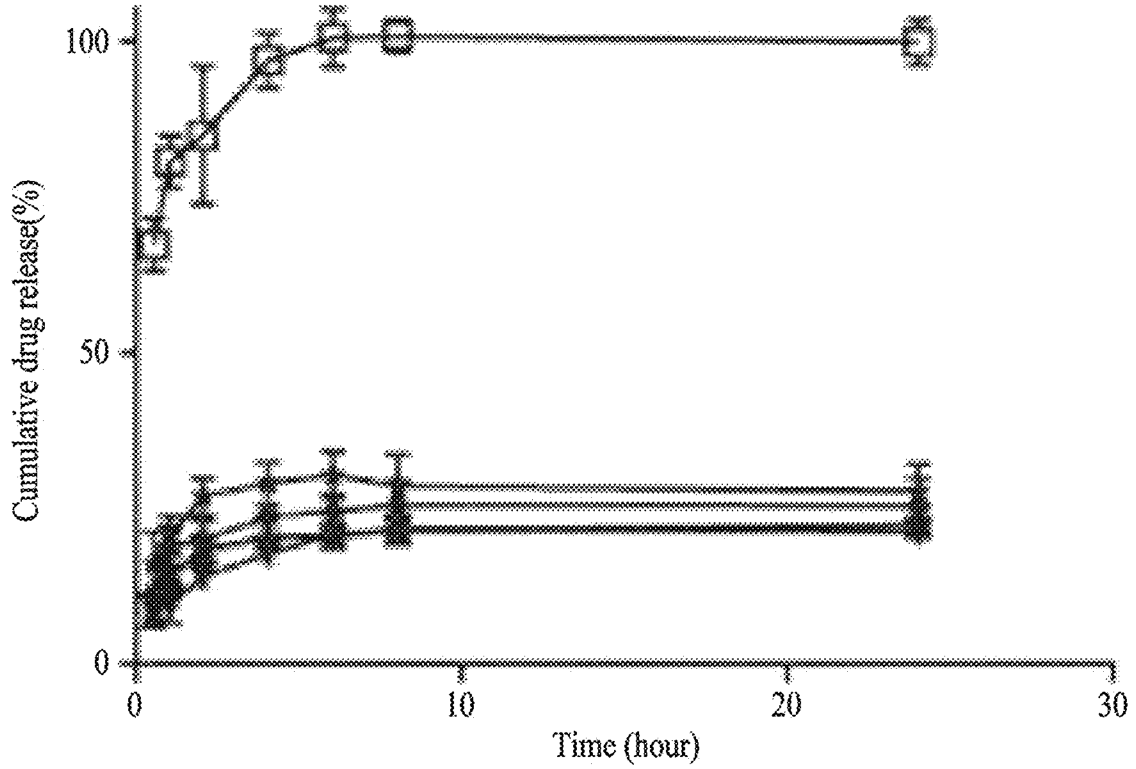
FIG. 2 is a diagram illustrating drug release patterns of drug pure substance powder (□), a drug-bentonite complex (■), a phospholipid-drug-bentonite complex with a weight ratio of 1:4:8 (▲), a phospholipid-drug-bentonite complex with a weight ratio of 2:4:8 (▼), a phospholipid-drug-bentonite complex with a weight ratio of 4:4:8 (♦) and a phospholipid-drug-bentonite complex with a weight ratio of 6:4:8 (★), when using a 0.1 N HCl solution (pH 1.2) as a release solution according to an example embodiment.
Figure 3:
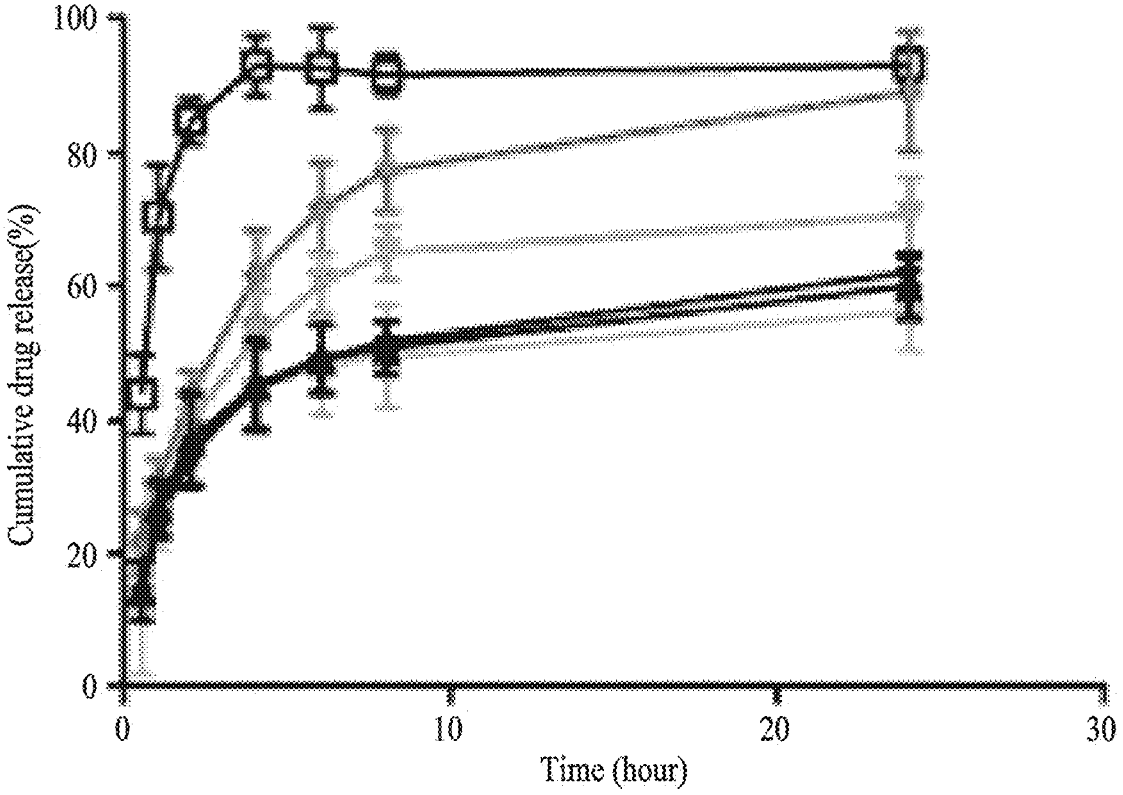
FIG. 3 is a diagram illustrating drug release patterns of drug pure substance powder (□), a drug-bentonite complex (■), a phospholipid-drug-bentonite complex with a weight ratio of 1:4:8 (▲), a phospholipid-drug-bentonite complex with a weight ratio of 2:4:8 (▼), a phospholipid-drug-bentonite complex with a weight ratio of 4:4:8 (♦) and a phospholipid-drug-bentonite complex with a weight ratio of 6:4:8 (★), when using a phosphate buffered saline (pH 7.4) as a release solution according to an example embodiment.

Experimental Example 3. Drug Release Behavior of Phospholipid-Drug-Bentonite Complex A drug release experiment using a semi-permeable membrane was conducted to confirm a drug release pattern from the phospholipid-drug-bentonite complex. A drug powder added with 2 mL of distilled water (drug powder), the drug-bentonite complex of Example Embodiment 1-3, and 2 mL of an aqueous dispersion of the phospholipid-drug-bentonite complexes of Example Embodiments 2-1 to 2-4 was added into a semi-permeable bag (molecular weight cut-off 12,000 to 14,000 Da) and immersed in 28 mL of a release solution, and then the drug concentration released from the outside of the membrane was measured to calculate a cumulative amount of the released drug over time. The amount of the drug-bentonite complex or the phospholipid-drug-bentonite complex was adjusted so that the final drug concentration in the release system was the same. At this time, as the release solution, a 0.1 N aqueous hydrochloric acid solution of pH 1.2 and phosphate buffered saline (pH 7.4) were used and the release was performed while maintaining 37° C. The experiment was conducted while taking a portion of the release solution outside the semi-permeable membrane at each time and replenishing the same amount of the release solution, the drug concentration of the collected sample was analyzed using HPLC, and the results were shown in FIGS. 2 and 3. FIG. 2 shows drug release amounts over time with respect to the drug powder, and the drug-bentonite complex and the phospholipid-drug-bentonite complex aqueous dispersions in a pH 1.2 environment, and FIG. 3 shows drug release amount over time with respect to the drug powder, the drug-bentonite complex, and the phospholipid-drug-bentonite complex aqueous dispersion in a pH 7.4 environment.

In the case of the drug powder, 50% or more of the drug was released within initial 1 hour in both the pH 1.2 and pH 7.4 environments, and most of the drug was released within 2 hours. In the case of the drug-bentonite complex aqueous dispersion, the drug was slowly released over about 24 hours in an acidic environment (pH 1.2), but the maximum release rate was also measured to be low (22.4±2.8%). Even in a neutral environment (pH 7.4), the drug was slowly released over about 24 hours, and the maximum release rate increased (56.3±5.9%) compared to the acidic environment.

On the other hand, in the case of the phospholipid-drug-bentonite complex aqueous dispersion, the drug was slowly released in an acidic environment, and the maximum release rate did not show a significant difference from that of a conventional drug-bentonite complex. Through this, since the phospholipid-drug-bentonite complex has an initial release delay effect of the drug-bentonite complex without containing the phospholipid, it may be inferred that the initial release in the upper digestive tract will be delayed, resulting in a sustained release. Meanwhile, in a neutral pH environment, there was a difference in drug release pattern between the drug-bentonite complex and the phospholipid-drug-bentonite complex. Unlike the drug powder, the initial release rate decreased, but the maximum release rate increased after 24 hours, and particularly, the phospholipid-drug-bentonite complex with a weight ratio of 4:4:8 showed the maximum release rate (89.2±9.0%) without a difference compared to the drug powder. That is, it may be seen that the low release rate of the drug-bentonite complex without the phospholipid has been improved.

Experimental Example 4. Morphological Characteristics of Phospholipid-Drug-Bentonite Complex In order to confirm the characteristics of the phospholipid-drug-bentonite complex of the present disclosure, the surface shapes of the bentonite, the phospholipid, the quetiapine, the drug-bentonite complex described in Example Embodiment 1-3, the phospholipid-bentonite complex described in Example Embodiment 2-1, the phospholipids-drug-bentonite complex described in Example Embodiment 2-3 were observed using a scanning electron microscope (SEM). The SEM image was photographed after adsorbing powdered samples to a copper tape and performing the platinum coating.

Figure 4:
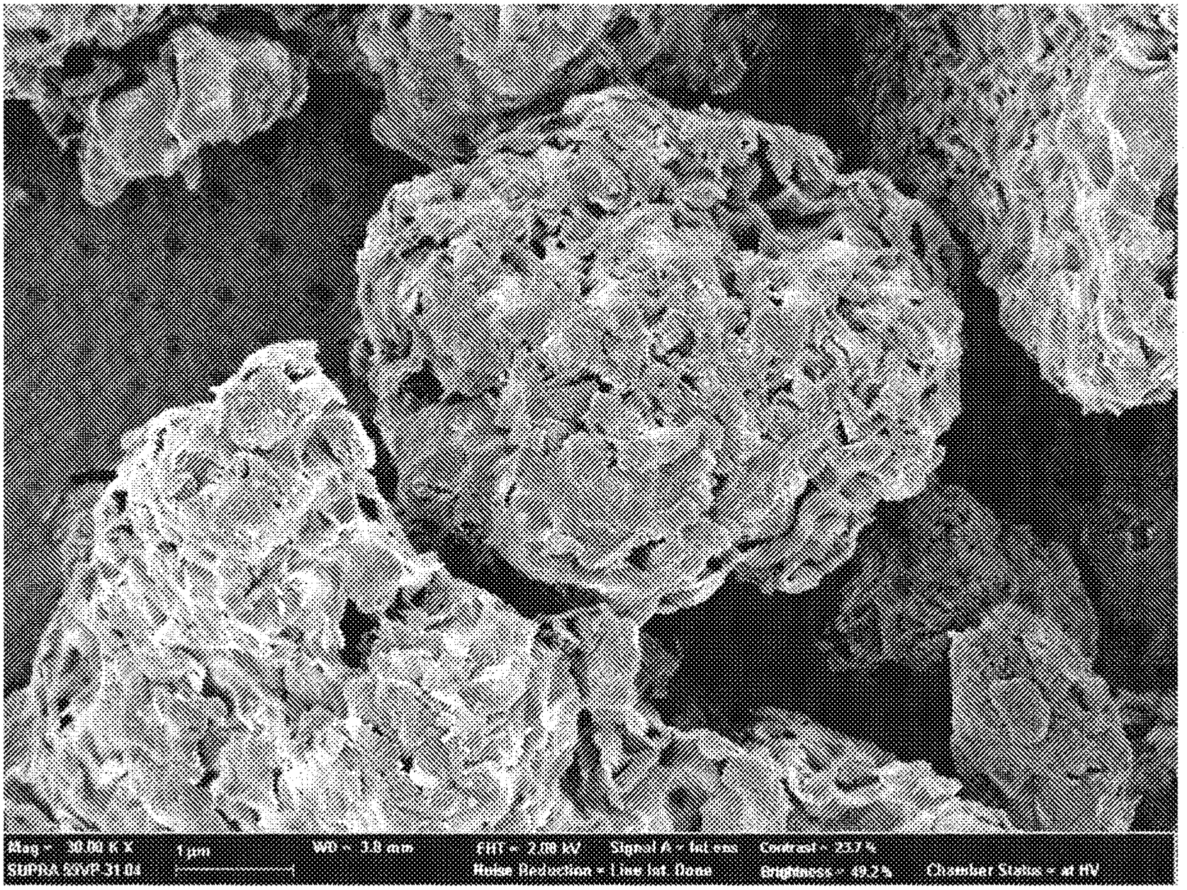
FIG. 4 is a diagram illustrating a scanning electron micrograph of bentonite according to an example embodiment.
Figure 5:
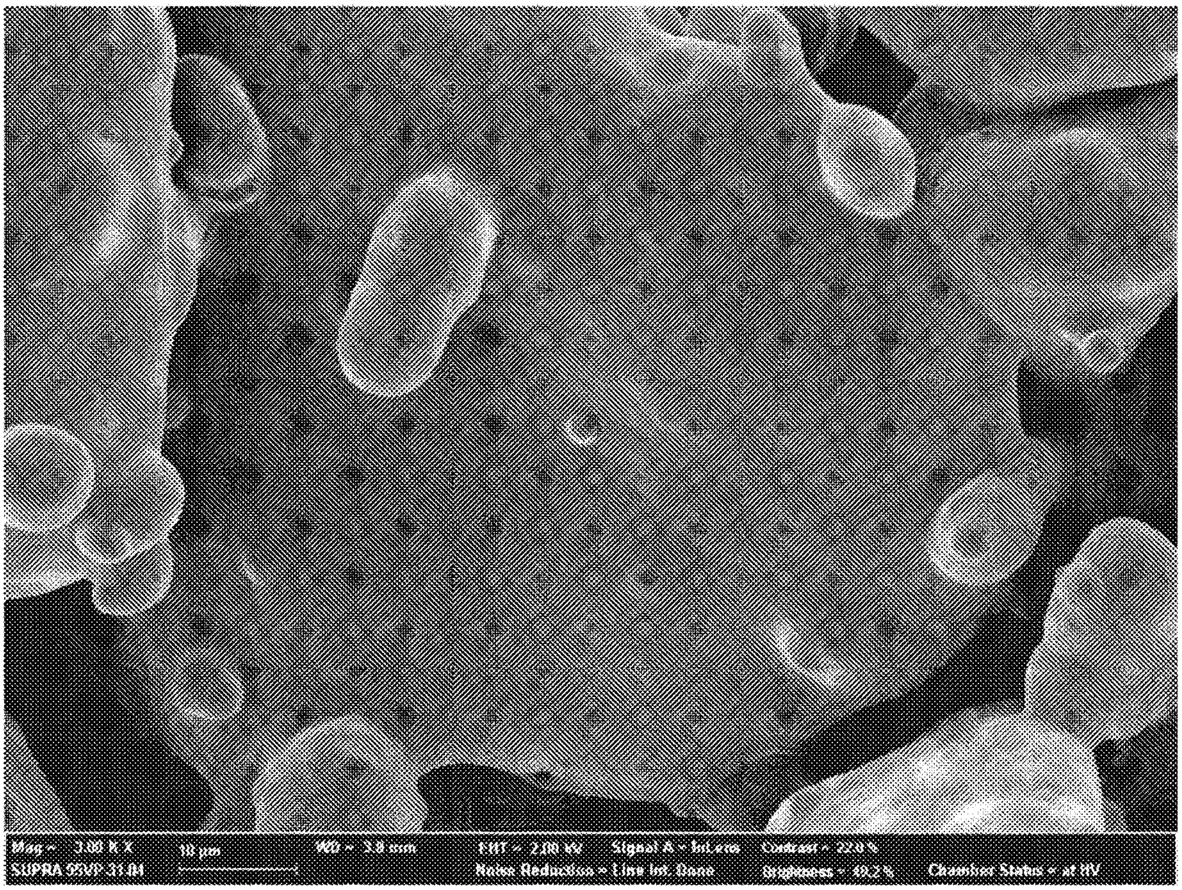
FIG. 5 is a diagram illustrating a scanning electron micrograph of a phospholipid according to an example embodiment.
Figure 6:
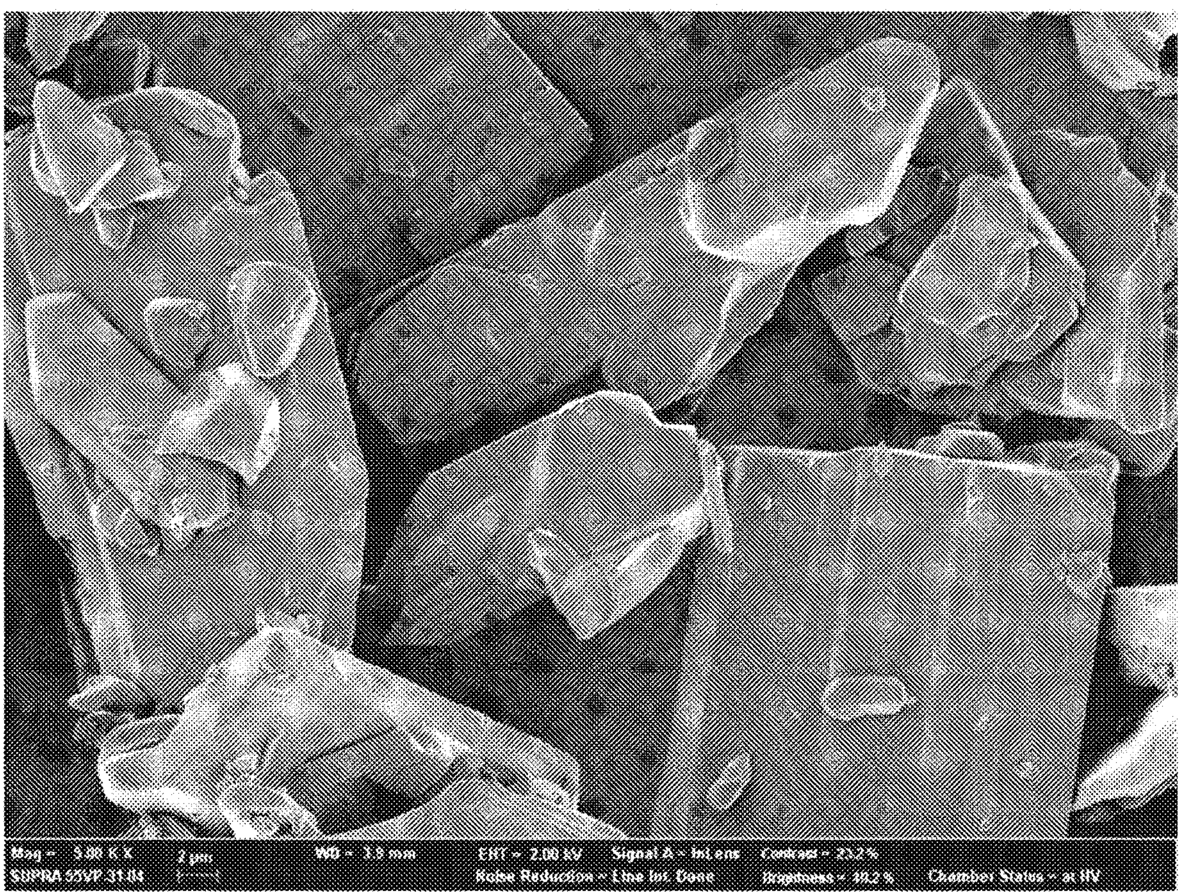
FIG. 6 is a diagram illustrating a scanning electron micrograph of a drug according to an example embodiment.
Figure 7:
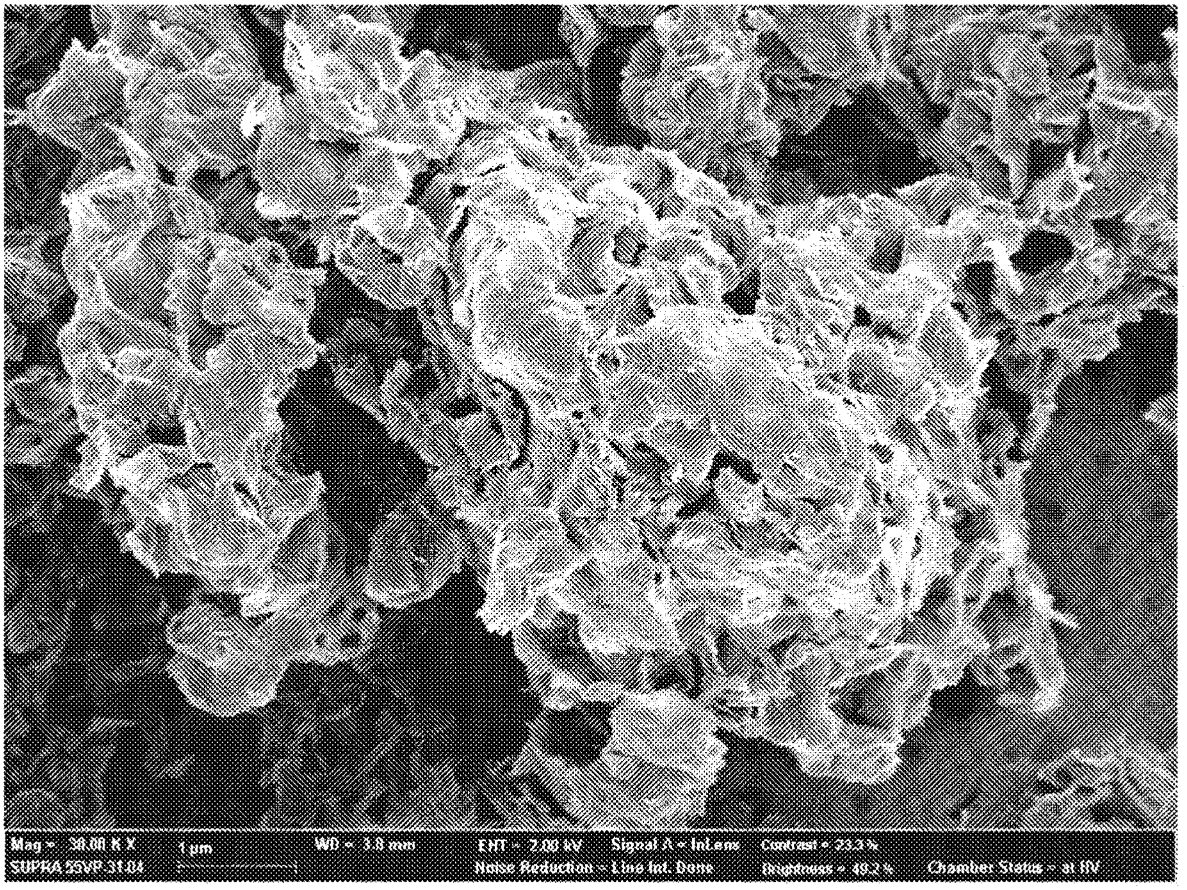
FIG. 7 is a diagram illustrating a scanning electron micrograph of a phospholipid-bentonite complex according to an example embodiment.
Figure 8:
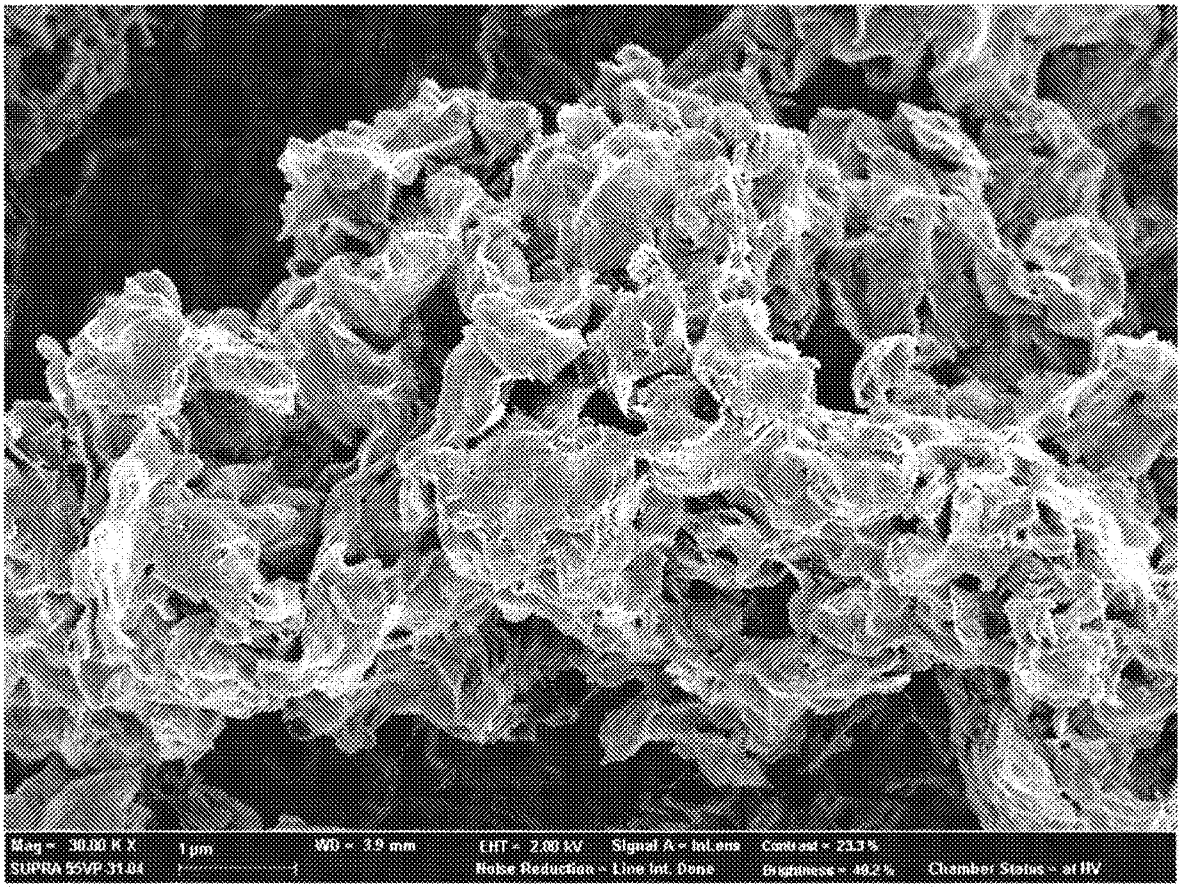
FIG. 8 is a diagram illustrating a scanning electron micrograph of a drug-bentonite complex according to an example embodiment.
Figure 9:
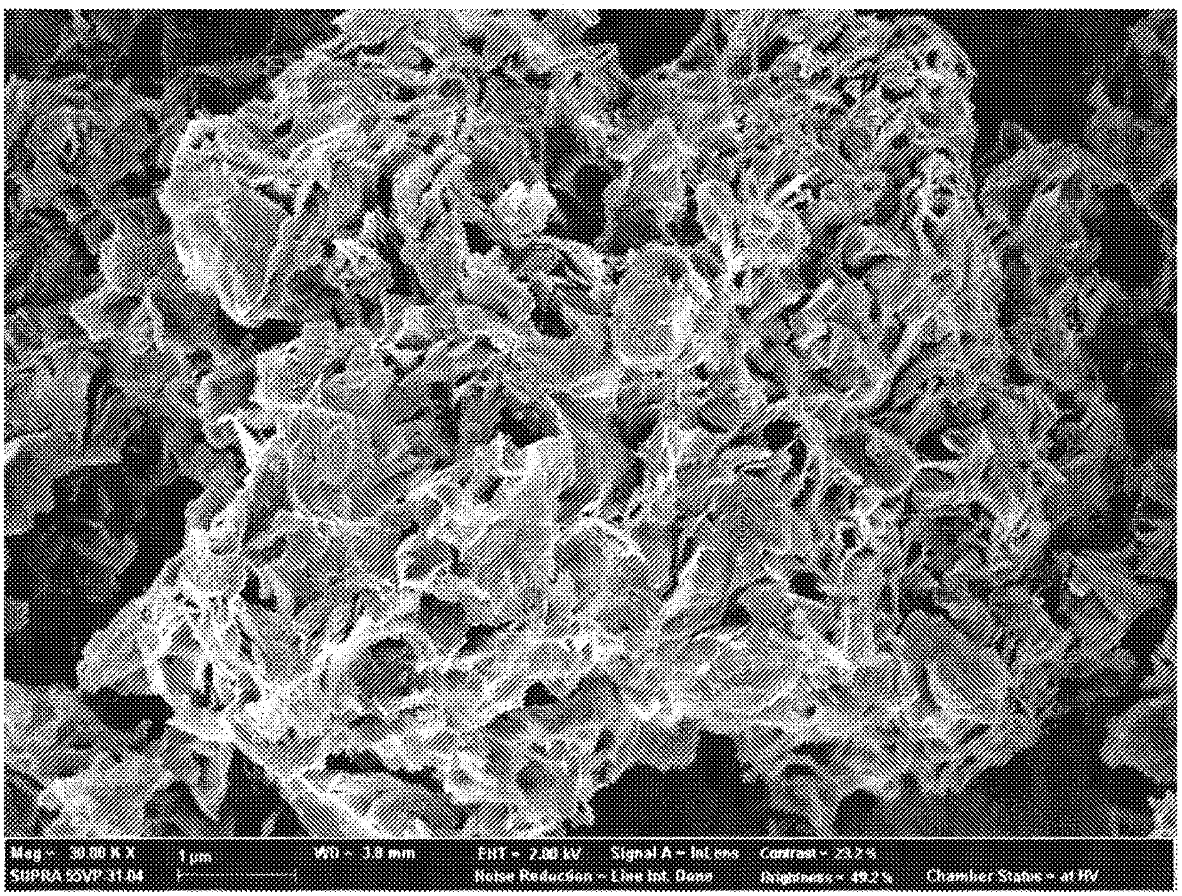
FIG. 9 is a diagram illustrating a scanning electron micrograph of a phospholipid-drug-bentonite complex according to an example embodiment.

Referring to FIGS. 4 to 6, it may be seen that the bentonite, the phospholipid, and the drug have different surface shapes, respectively, and referring to FIGS. 7 to 9, it may be seen that the SEM images obtained by observing the surface shapes of the phospholipid-bentonite, the drug-bentonite complex, and the phospholipid-drug-bentonite are almost the same as the shape of the bentonite.

Figure 10:
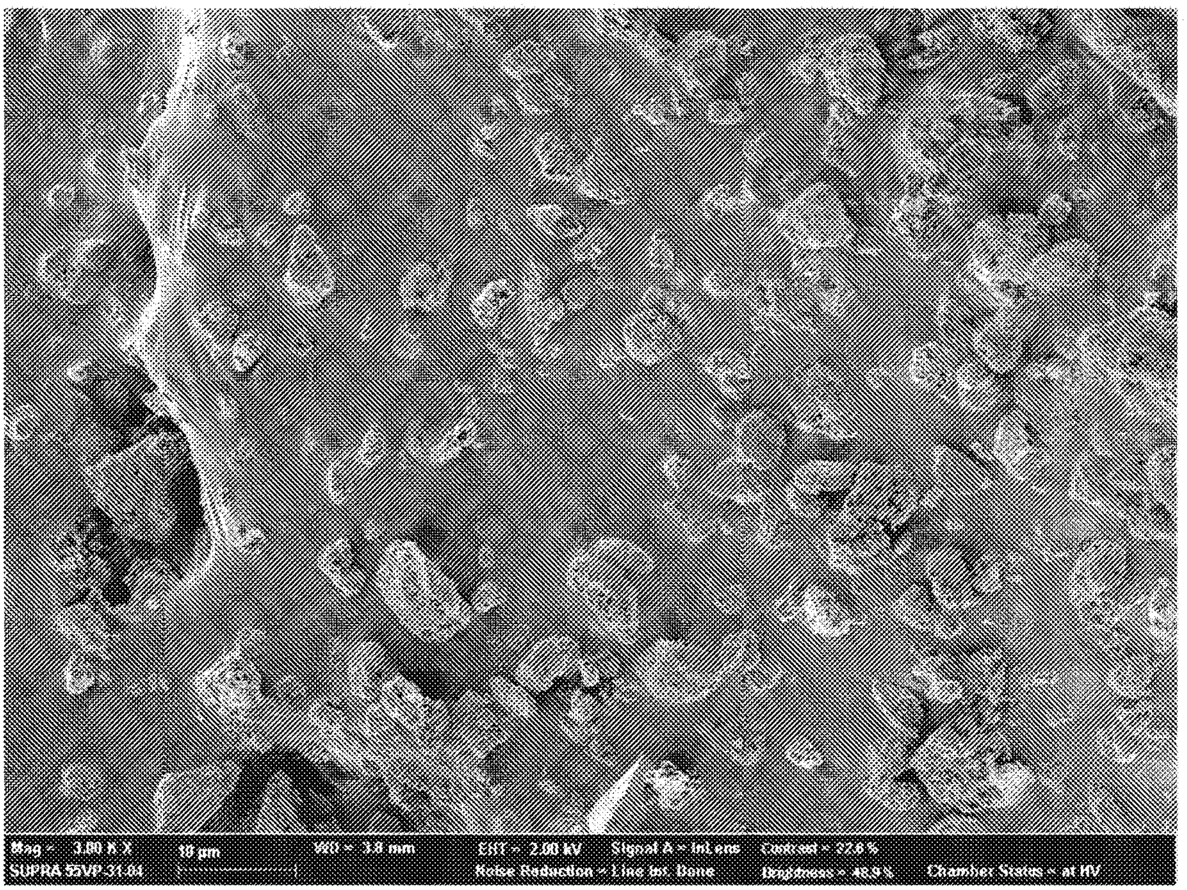
FIG. 10 is a diagram illustrating a scanning electron micrograph of a physical mixture of a phospholipid and bentonite according to an example embodiment.
Figure 11:
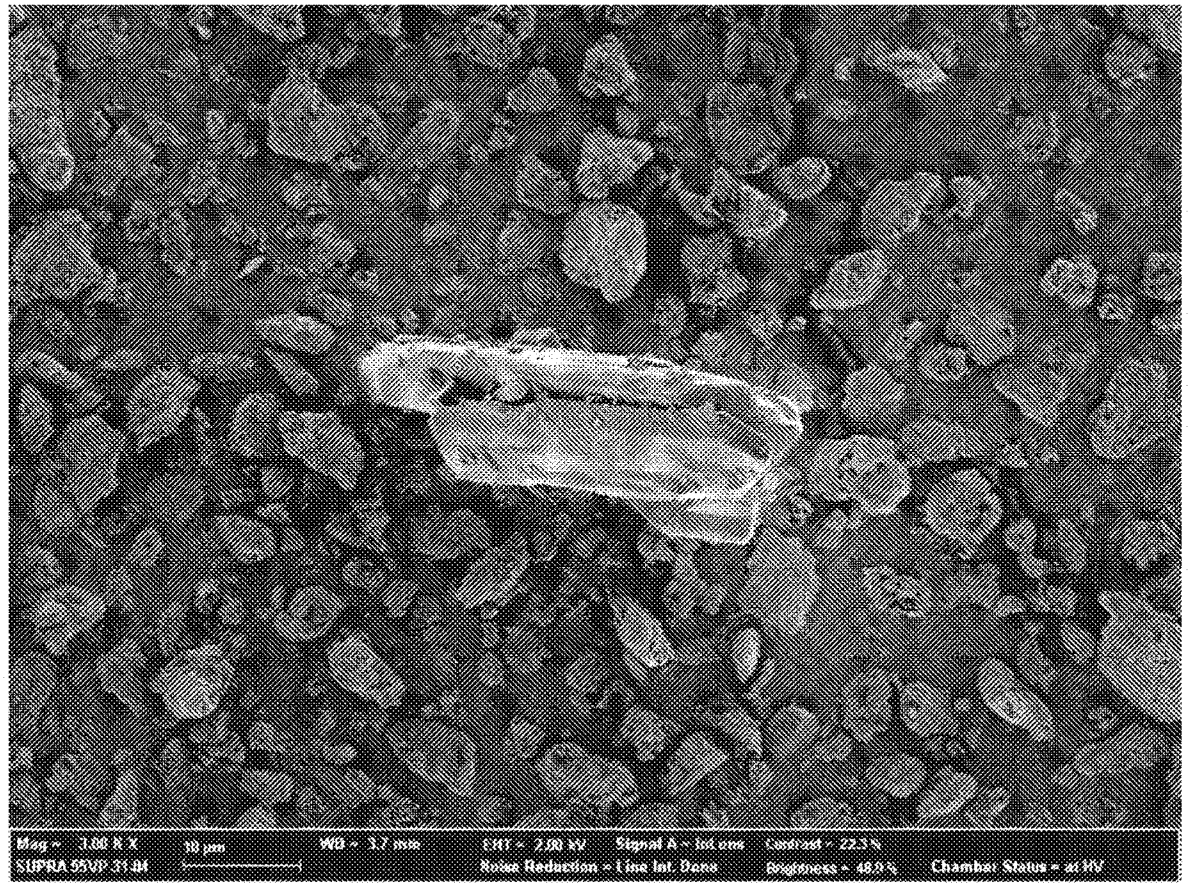
FIG. 11 is a diagram illustrating a scanning electron micrograph of a physical mixture of a drug and bentonite according to an example embodiment.

As a result, it may be seen that when the phospholipids and the drug are adsorbed to the bentonite, the phospholipids and the drug are adsorbed within the layered structure of the bentonite, and the drug is adsorbed in an amorphous form. It may also be confirmed that the surface forms of the constituent materials are observed together in FIGS. 10 and 11, in which the surface forms of the physical mixtures (Comparative Examples 1 and 2) were observed.

Experimental Example 5. Crystallographic Characteristics of Phospholipid-Drug-Bentonite Complex In order to confirm the crystallographic characteristics of the phospholipid-drug-bentonite complex of the present disclosure, X-ray diffraction analysis was used, and the results were shown in FIG. 12. For X-ray diffraction analysis, a D8 ADVANCE model from Brucker Co., Ltd. was used, and a copper cathode was used as an X-ray source. The wavelength of the X-ray was 1.5418 Å (40 kV, 40 mA conditions) and the analysis was performed in a 2θ range of 2 to 40 (0.5 sec/step).

Figure 12:
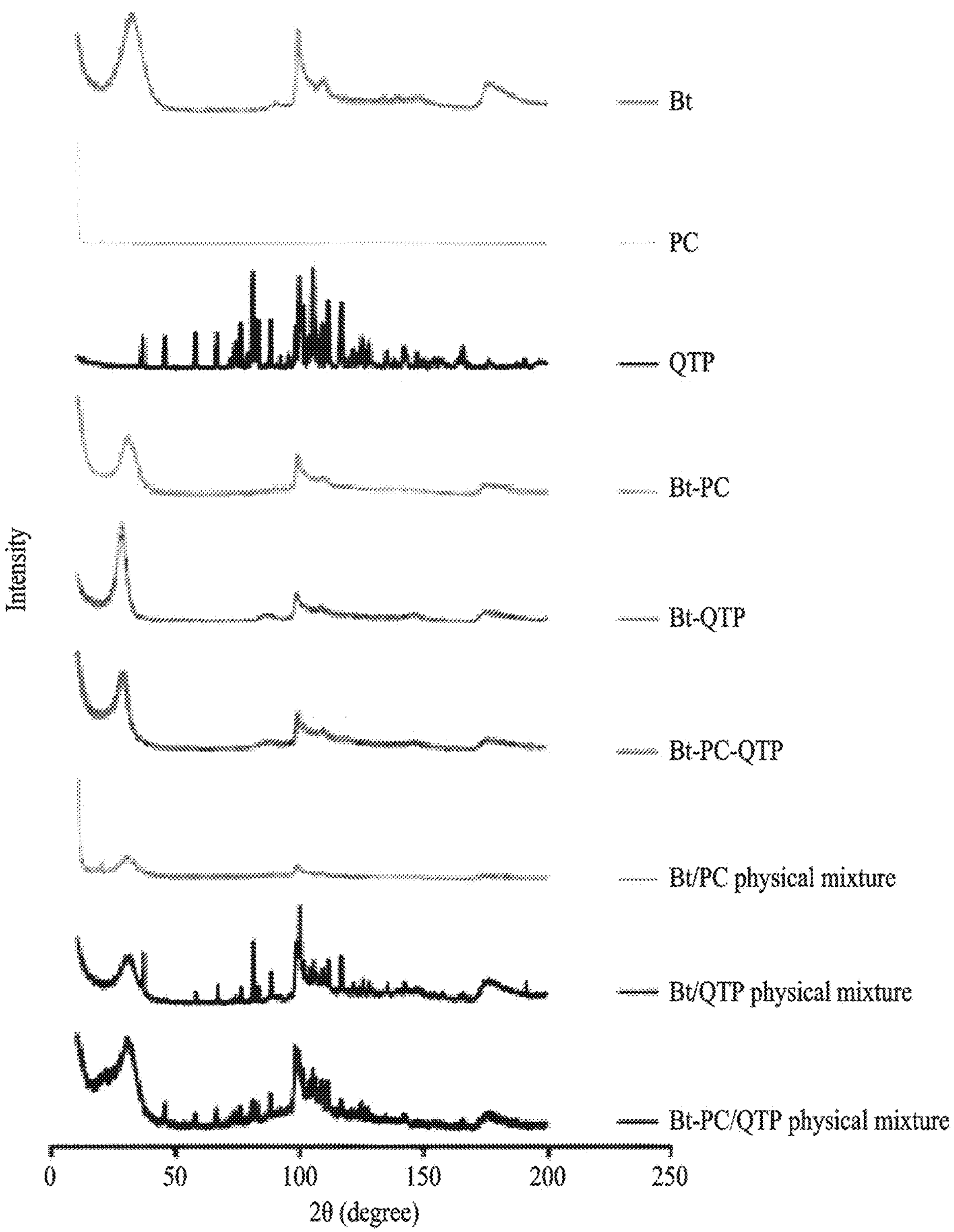
FIG. 12 is a diagram illustrating X-ray diffraction analysis results for bentonite (Bt), a phospholipid (PC), a drug (QTP), a phospholipid-bentonite complex (Bt-PC), a drug-bentonite complex (Bt-QTP), a phospholipid-drug-bentonite complex (Bt-PC-QTP), a physical mixture of a phospholipid and bentonite (Bt/PC physical mixture), a physical mixture of a drug and bentonite (Bt/QTP physical mixture), and a physical mixture of a drug and phospholipid-bentonite (Bt-PC/QTP physical mixture) according to an example embodiment.

Referring to FIG. 12, in the X-ray diffraction analysis of physical mixtures (Comparative Examples 1, 2, and 3), main peaks due to the specific crystal structures observed in drug compounds and specific main peaks observed in phospholipids were observed relatively clearly. However, it may be seen that only the X-ray diffraction peak of bentonite is observed in phospholipid-bentonite in which a phospholipid or drug is adsorbed to bentonite (Example Embodiment 2-1), a drug-bentonite complex (Example Embodiment 1-3) or a phospholipid-drug-bentonite complex (Example Embodiment 2-3). That is, it may be seen that the drug exists in an amorphous state when forming a complex with bentonite, and when the drug and the phospholipid are adsorbed to bentonite, the drug and the phospholipids are not physically mixed, but adsorbed within the layered structure of bentonite.

Figure 13:
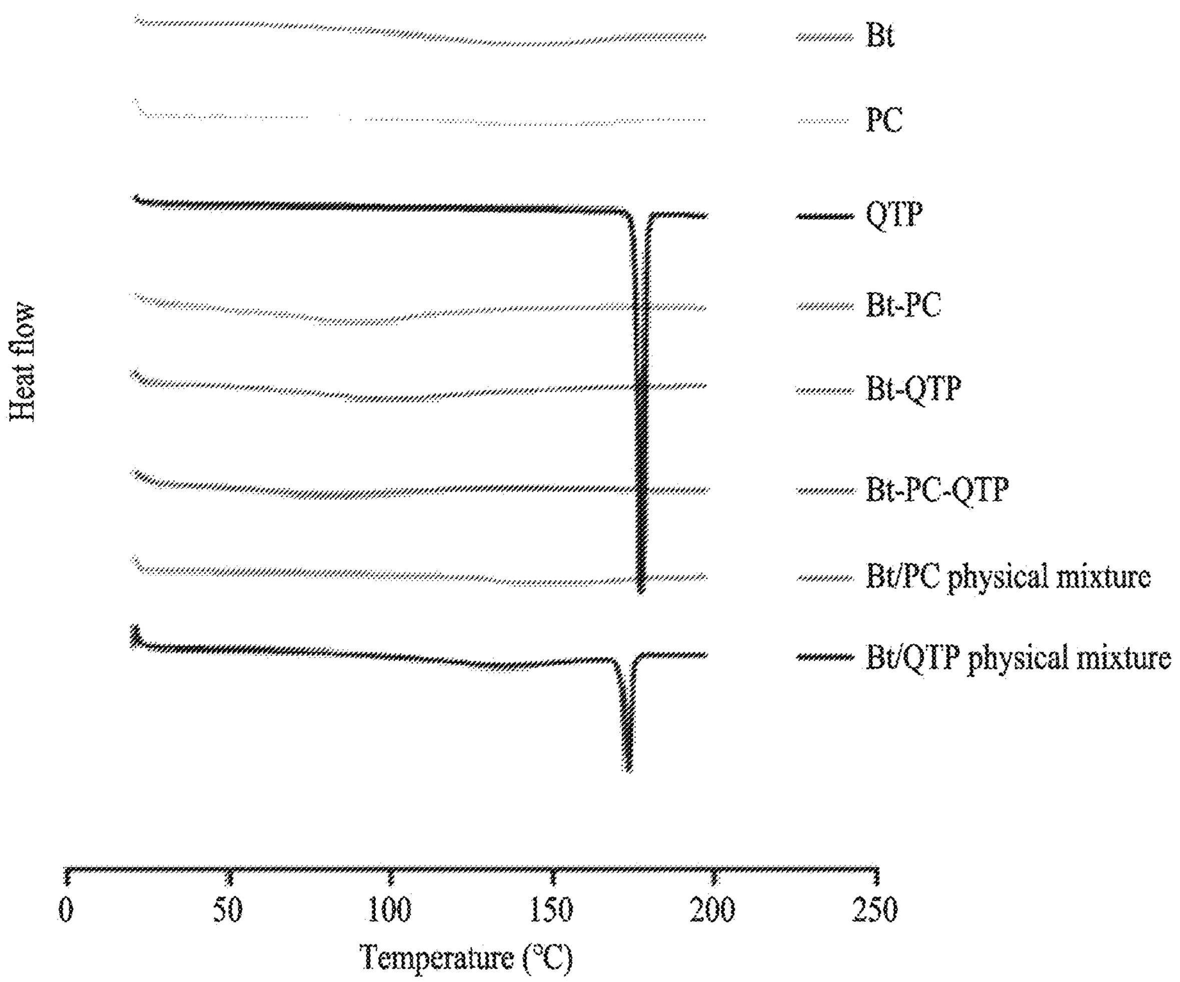
FIG. 13 is a diagram illustrating DSC analysis results for bentonite (Bt), a phospholipid (PC), a drug (QTP), a phospholipid-bentonite complex (Bt-PC), a drug-bentonite complex (Bt-QTP), a phospholipid-drug-bentonite complex (Bt-PC-QTP), a physical mixture of a phospholipid and bentonite (Bt/PC physical mixture), and a physical mixture of a drug and bentonite (Bt/QTP physical mixture) according to an example embodiment.

Experimental Example 6. Amorphous Adsorption of Drug in Phospholipid-Drug-Bentonite Complex In order to confirm that the drug exists in an amorphous state in the phospholipid-drug-bentonite complex of the present disclosure, DSC analysis was performed, and the results were shown in FIG. 13. For DSC analysis, a Discovery DSC model from TA Instrument Co., Ltd. was used, and measurement was performed while increasing the temperature in the range of 20° C. to 200° C. at a rate of 10° C./min. Referring to FIG. 13, in a differential scanning calorimetry for the drug, a characteristic peak due to an endothermic reaction was observed, and even in the DSC analysis of the physical mixture (Comparative Example 1), a characteristic peak observed in the drug was observed relatively clearly. However, it may be seen that since the characteristic peak observed in the drug was not observed in the drug-bentonite complex (Example Embodiment 1-3) or the phospholipid-drug-bentonite complex (Example Embodiment 2-3), the drug compound exists in an amorphous state when forming a complex with bentonite.

Experimental Example 7. Pharmacokinetic Characteristics of Phospholipid-Drug-Bentonite Complex In order to evaluate the pharmacokinetic characteristics of the phospholipid-drug-bentonite complex of the present disclosure, the phospholipid-drug-bentonite complex was orally administered to rats as a subject, and then the trend of blood concentration over time was observed. After the femoral regions of the fixed rats were shaved, the blood-gathering was prepared by injecting a cannula. An experimental group was used with a formulation in which the phospholipid-drug-bentonite complex of Example Embodiment 2-3 was filled in a capsule, and a control group was used with a formulation in which quetiapine and the drug-bentonite complex of Example Embodiment 1-3 were filled in capsules, respectively. After administering the capsules with an oral zonde for oral administration and immediately administering 1 mL of distilled water, a predetermined amount of blood was collected through a cannula for each predetermined time to measure the blood drug concentration.

Figure 14:
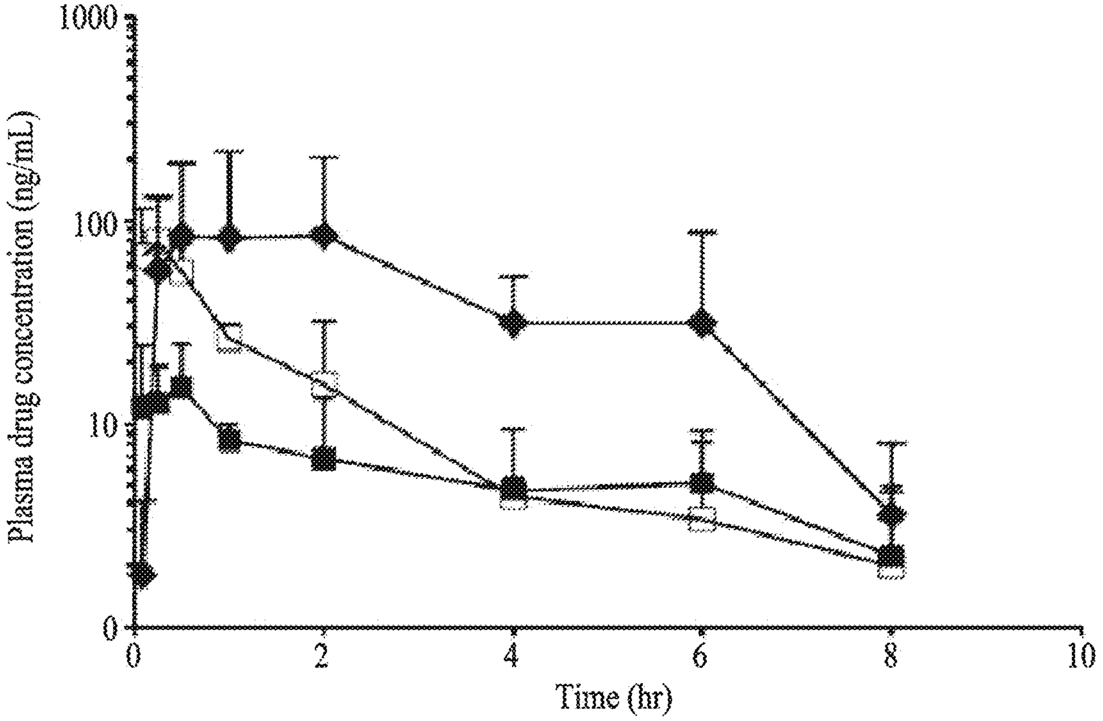
FIG. 14 is a diagram illustrating a blood drug concentration-time curve obtained after oral administration of a pure drug substance (□), a drug-bentonite complex (□), and a phospholipid-drug-bentonite complex (♦) filled in capsule formulations according to an example embodiment.

In the case of the drug (quetiapine), the drug-bentonite complex, and the phospholipid-drug-bentonite complex, 5 mg/kg was orally administered as a drug dose, and the drug concentrations in blood samples were analyzed by a mass spectrometry to determine a blood drug concentration-time curve (see FIG. 14). Table 3 showed pharmacokinetic parameters calculated by examining the in vivo kinetic characteristics of the drug using the blood drug concentration-time curve shown in FIG. 14. The pharmacokinetic parameters were calculated using a non-compartment model of a WinNonlin program (Version 3.1) based on blood drug concentration-time values. $AUC_{last}$ was obtained by calculating an area under the curve through a linear trapezoidal method from a time taken when a first concentration was measured to a time taken when the last concentration was measured, and $AUC_{inf}$ was obtained by extrapolating the blood concentration-time curve from the time taken when the last concentration was measured to an infinity time and then calculating an area under the blood concentration-time curve. The oral bioavailability of the bentonite complex was calculated using Formula of [$AUC_{inf}$ (bentonite complex)/$AUC_{inf}$(quetiapine)*100].

TABLE 3

| Pharmacokinetic parameter | Quetiapine | Drug-bentonite complex (Example Embodiment 1-3) | Phospholipid-drug-bentonite complex (Example Embodiment 2-3) |
|---|---|---|---|
| Administered drug dose (mg/kg) | | 5 | |
| Half-life (hr) | 1.6 ± 0.5 | 4.4 ± 1.4 | 4.7 ± 1.9 |
| C max (ng/mL) | 105.8 ± 31.4 | 21.5 ± 8.5 | 225.3 ± 76.9 |
| AUC last (ng · hr/mL) | 107.4 ± 15.7 | 48.5 ± 11.7 | 381.7 ± 94.2 |
| AUC inf (ng · hr/mL) | 114.7 ± 20.9 | 83.1 ± 10.9 | 442.4 ± 129.5 |
| Oral bioavailability (%) | 100 | 72 | 386 |

As a result, referring to FIG. 14, it may be confirmed that in the case of quetiapine capsules, the oral bioavailability reaches a maximum blood concentration (Cmax) within 15 minutes to 1 hour after oral administration, and then reaches a lose step in which the blood drug concentration rapidly decreases. On the other hand, the drug-bentonite complex showed a relatively low maximum blood concentration (21.5±8.5 ng/ml), and even after 8 hours of oral administration, a constant blood drug concentration was observed, and the half-life was also longer than a half-life (4.4±1.4) of the quetiapine capsule. However, considering that a drug therapeutic index of quetiapine is 70 to 170 ng/mL, the existing drug-bentonite complex is expected to have a low therapeutic effect. On the other hand, in the case of the phospholipid-drug-bentonite complex of the present disclosure, the maximum blood concentration (225.3±76.9) was higher due to a solubilization effect of the phospholipid, and the high blood drug concentration was maintained for 6 hours or more. Accordingly, since the complex of the present disclosure may maintain the blood drug concentration close to the therapeutic index while preventing the initial blood concentration from rapidly increasing, it may be expected to have the greatest therapeutic effect. Furthermore, in terms of oral bioavailability (%) derived through the $AUC_{inf}$ value, the phospholipid-drug-bentonite complex of the present disclosure showed the highest bioavailability. In the case of quetiapine, the drug was precipitated due to a rather high dose of the drug in the in vivo environment of the rats, so that much drug absorption was not observed in the intestinal environment. In addition, the drug-bentonite complex could maintain a constant blood drug concentration, but the blood drug concentration was low. Unlike this, it was confirmed that the phospholipid-drug-bentonite complex of the present disclosure shows much drug absorption in the intestinal environment due to the solubilization effect of the phospholipid, and compared to the control group, the oral bioavailability increased by about 3.8 times or more. From this, it may be concluded that it is appropriate to introduce a phospholipid as a method for improving the low bioavailability of a conventional drug-bentonite complex without containing a phospholipid.

Experimental Example 8. Evaluation of Drug Sustained Release Characteristic Maintaining Capacity of Phospholipid In order to confirm that the characteristics of a phospholipid that maintain the drug sustained release characteristics of bentonite were not shown in other types of surfactants, PEG2000-bentonite was prepared using polyethylene glycol 2000 (hereinafter, referred to as a hydrophilic solubilizer), which was a representative hydrophilic surfactant.

A PEG2000 solution was prepared by dissolving 10 mg of PEG2000 in a solvent mixed with distilled water and a 0.1 N aqueous hydrochloric acid solution, and a bentonite suspension was prepared by suspending bentonite powder of 4 times the mass of PEG2000 in the solvent mixed with the 0.1 N aqueous hydrochloric acid solution and distilled water. The PEG2000 solution and the bentonite suspension were mixed and then stirred for about 4 hours to prepare PEG2000-bentonite. At this time, a method of adding the bentonite suspension to the PEG200 solution under continuous stirring was used to prevent the bentonite powder from precipitating. Subsequently, the PEG2000-bentonite solution was centrifuged at 4,000 rpm for 10 minutes to precipitate the PEG2000-bentonite, and a supernatant was removed, and then the remaining pellets were rapidly cooled using liquid nitrogen and lyophilized to evaporate fully the remaining solvent. Next, using the mass of the quetiapine compound corresponding to 0.5 times the mass of the bentonite powder, which was a ratio optimized through Experimental Example 1, in the same manner described in Example 2-1, a hydrophilic solubilizer-drug-bentonite complex was prepared in a weight ratio of the hydrophilic solubilizer, the drug, and the bentonite of 1:2:4.

The drug content per complex unit weight of the prepared hydrophilic solubilizer-drug-bentonite complex was confirmed. The drug content was measured using the method described in Experimental Example 1, and the results were shown in Table 4.

TABLE 4

| Weight ratio of hydrophilic Solubilizer:drug:bentonite | Drug content (%) per unit weight |
|---|---|
| 1:2:4 | 13.7 ± 0.5 |

Figure 15:
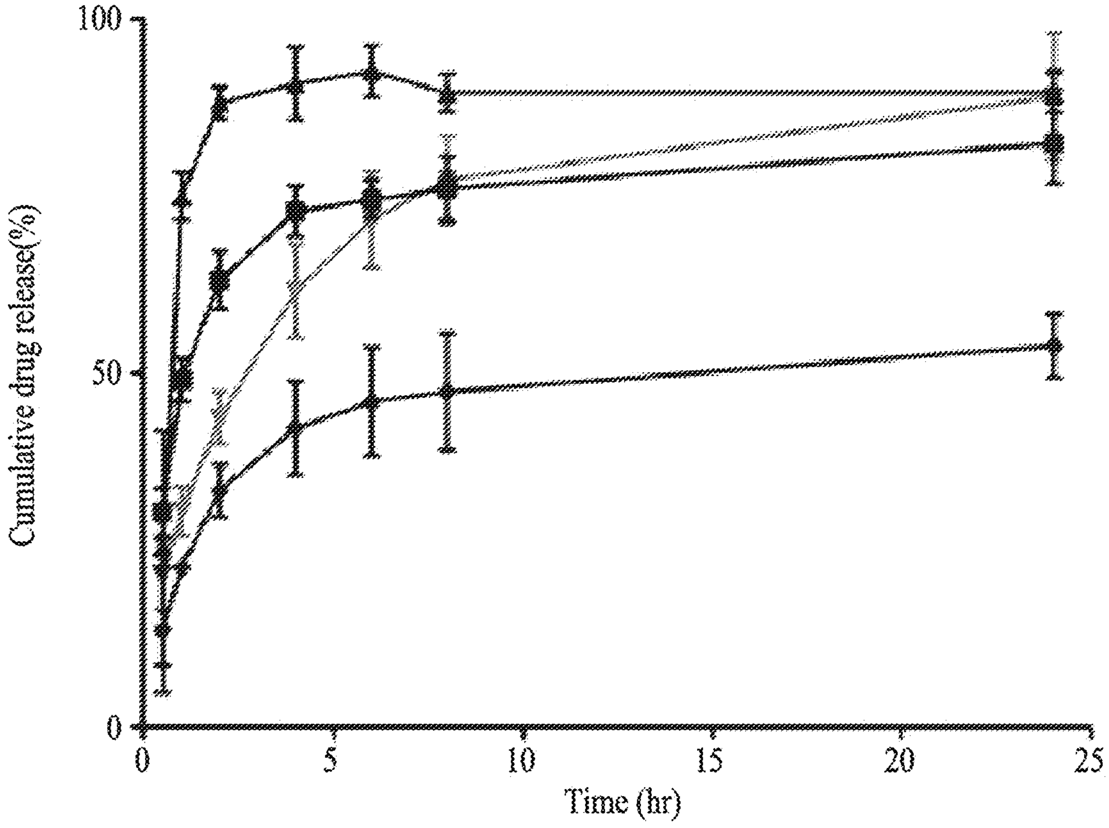
FIG. 15 is a diagram illustrating drug release patterns of drug powder (●), a drug-bentonite complex (□), a phospholipid-drug-bentonite complex with a weight ratio of 4:4:8 (♦), and a hydrophilic solubilizer-drug-bentonite complex (○) with a weight ratio of 1:2:4 by setting a phosphate buffered saline (pH 7.4) as a release solution according to an example embodiment.

Next, in order to compare the drug release patterns of the hydrophilic solubilizer-drug-bentonite and the phospholipid-drug-bentonite complex of the present disclosure (Example Embodiment 2-3), a release test was performed on phosphate buffered saline (pH 7.4) using the method described in Experimental Example 3, and the drug released amounts over time were measured. As a result, as illustrated in FIG. 15, in the case of the hydrophilic solubilizer-drug-bentonite complex, it was observed that the initial drug release increased compared to the phospholipid-drug-bentonite complex of the present disclosure, which maintained sustained release. In particular, the drug release after 2 hours was about 63%, which showed an increased release compared to the phospholipid-drug-bentonite complex of the present disclosure (about 43% after 2 hours). The additionally released drug from 4 hours to 24 hours showed a low release pattern of about 10% compared to the phospholipid-drug-bentonite complex.

Meanwhile, the total drug release rate after 24 hours was confirmed to be lower in the hydrophilic solubilizer-drug-bentonite complex than that in the phospholipid-drug-bentonite complex of the present disclosure. When a hydrophilic surfactant such as PEG2000 is used, it may be seen that the initial drug release is increased, and the late drug release is decreased compared to conventional drug-bentonite complexes without containing surfactants such as phospholipids. That is, when a hydrophilic surfactant is used, there is a problem in that the drug sustained release characteristics of the drug-bentonite complex disappear. In addition, unlike the phospholipid-drug-bentonite complex of the present disclosure, it was shown that the maximum drug release rate was low.

Therefore, in order to increase the oral bioavailability while maintaining the sustained release of the drug-bentonite complex, it is preferable to use lipid surfactants such as phosphatidylcholine rather than the hydrophilic surfactant.

Experimental Example 9. Drug Release Characteristics of Complex of Drug Having Amine Group and Bentonite

Experimental Example 9-1. Docetaxel

In the following solvent composition, a drug adsorption reaction was performed by setting DMSO: acetonitrile: 0.1 N HCl=0.15:0.05:0.80, fixing the concentration of docetaxel (Taihua Co. (Xi'an, China)) to 0.5 mg/mL, and applying different concentrations (0.5, 1, 1.5, 2.5, and 5 mg/mL) of bentonite, and as a result, the highest drug adsorption rate was shown when the weight ratio of docetaxel and bentonite was 1:2.

TABLE 5

| Weight ratio of docetaxel:bentonite | Drug adsorption rate (%) |
|---|---|
| 1:1 | 62.0 ± 17.3 |
| 1:2 | 74.5 ± 11.8 |
| 1:3 | 28.9 ± 25.3 |
| 1:5 | 65.8 ± 23.6 |
| 1:10 | 52.8 ± 18.5 |

Experimental Example 9-2. Ciprofloxacin

Figure 16:
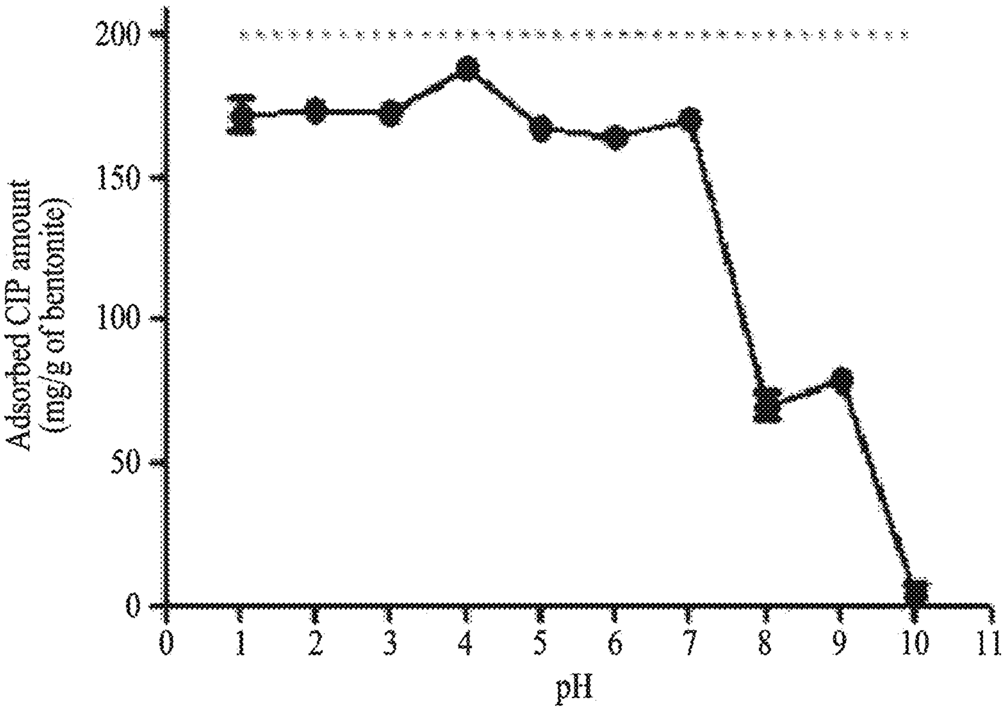
FIG. 16 is a diagram illustrating an adsorbed amount of ciprofloxacin in bentonite according to pH according to an example embodiment.
Figure 17:
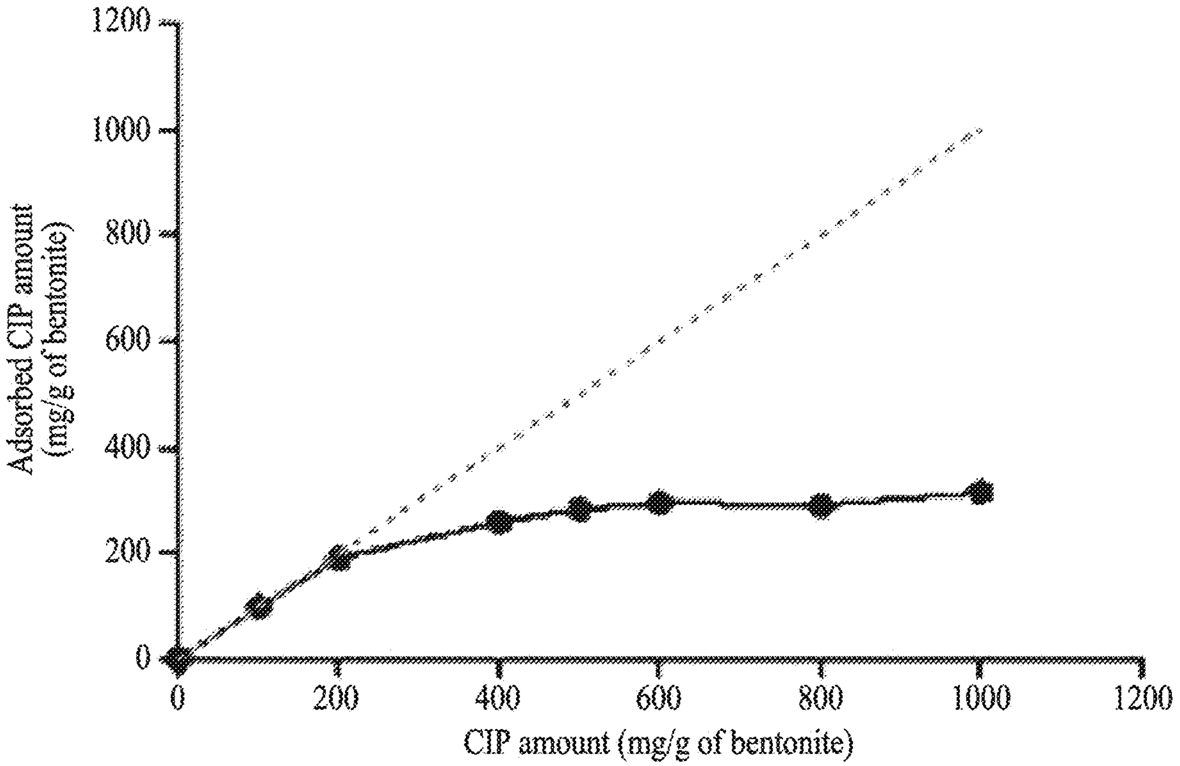
FIG. 17 is a diagram illustrating an adsorbed amount of ciprofloxacin to a bentonite mass according to a concentration change of ciprofloxacin according to an example embodiment.
Figure 18:
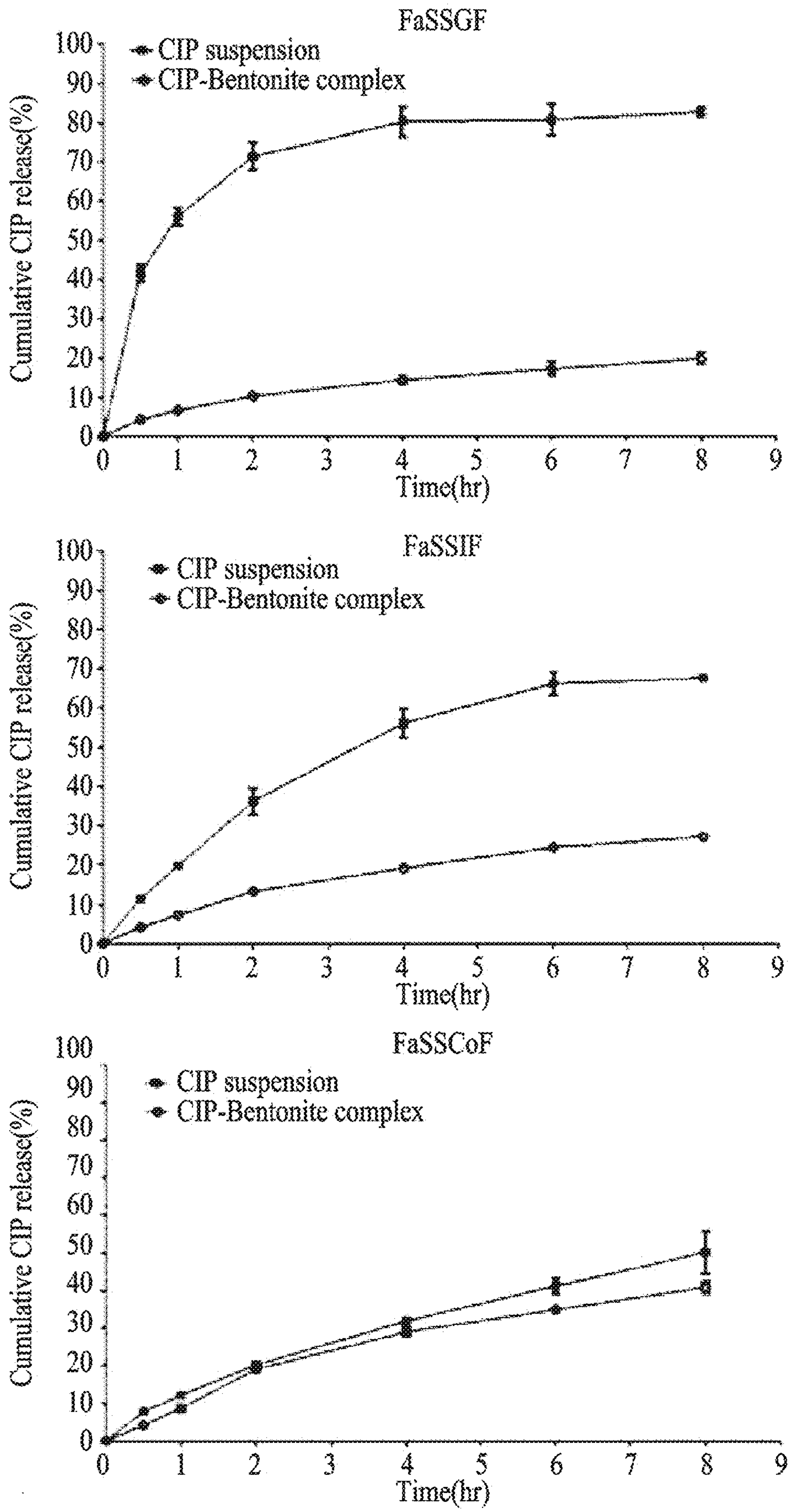
FIG. 18 is a diagram illustrating a release pattern of a ciprofloxacin-bentonite complex under FaSSGF (simulated gastric fluid), FaSSIF (simulated small intestine fluid), and FaSSCoF (simulated colon fluid) conditions according to an example embodiment.

The concentrations of ciprofloxacin (Tokyo Chemical Industry, TCI) and bentonite were set to 0.5 mg/mL and 5 mg/mL, respectively, and a ciprofloxacin-bentonite complex was prepared according to the method described in Example Embodiment 1-1 above. As a result of monitoring the adsorption amount of ciprofloxacin in the complex prepared in a pH range of 1 to 10, high adsorption was shown from pH 1 to pH 7, and the adsorption decreased at pH conditions exceeding pH 7, which was a neutral condition (see FIG. 16). Based on the above results, as a result of reacting a predetermined concentration of bentonite (0.5 mg/mL) with different concentrations (50, 100, 150, 200, 300, 400, and 500 μg/mL) of ciprofloxacin at pH 1, it was confirmed that the amount of drug adsorption was difficult to exceed 300 mg/g (see FIG. 17). Therefore, when the weight ratio of ciprofloxacin and bentonite was 1:5, a drug adsorption rate close to 100% may be achieved while minimizing the used amount of bentonite, and accordingly, a drug release pattern according to pH was confirmed using a complex in which the weight ratio of ciprofloxacin and bentonite was 1:5. The release pattern according to the pH of the complex was confirmed through a release test using a dialysis membrane. As a result, as shown in FIG. 18, in a group in which a ciprofloxacin compound was suspended, the drug was rapidly released under FaSSGF (simulated gastric fluid) conditions with high solubility, and a decreasing trend in the total released amount was shown toward FaSSIF (simulated small intestine fluid) and FaSSCoF (simulated colon fluid). On the other hand, in the ciprofloxacin-bentonite complex group, it was confirmed that the released amount was increased in the order of FaSSGF, FaSSIF, and FaSSCoF, so that the ciprofloxacin-bentonite complex released the drug in a pH-dependent manner.

Experimental Example 9-3. Camptothecin

The concentration of camptothecin (Tokyo Chemical Industry, TCI) was made at 0.25 mg/mL using a 100% 1 N HCl solvent and the drug and bentonite reacted with each other at various ratios shown in Table 6 below, and then the drug amount adsorbed to bentonite was indirectly measured by measuring the drug concentration of the supernatant.

TABLE 6

| Campto-thecin-bentonite ratio | Supernatant concentration (μg/mL) | Drug adsorption rate (%) | Adsorption amount (mg) of camptothecin per 1 g of bentonite |
|---|---|---|---|
| 1:0 | 49.7 ± 0.3 | — | — |
| 1:1 | 50.1 ± 0.5 | 80.0 ± 0.2 | — |
| 1:2 | 50.2 ± 0.6 | 79.9 ± 0.2 | — |
| 1:5 | 46.2 ± 0.5 | 81.5 ± 0.2 | — |
| 1:10 | 12.4 ± 0.3 | 95.0 ± 0.1 | 95.0 ± 0.1 |
| 1:20 | 3.2 ± 0.1 | 98.7 ± 0.0 | 49.4 ± 0.0 |

As a result, when the weight ratio of camptothecin and bentonite was 1:10, the adsorption rate was 95% or more, and it was inferred that most drugs were bound to bentonite by ionic interaction without undissolved drug crystals. As a result of preparing the camptothecin-bentonite complex under the condition of 1:10, the yield was calculated as 84.1±0.5%.

Experimental Example 9-4. Carbamazepine

Carbamazepine (please indicate a purchase place) at a concentration of 0.5 mg/mL and bentonite reacted with each other in a weight ratio of 1:1, 1:2, 1:3, 1:5, and 1:10 in a solvent of ACN 5% and 1 N HCl 95% and the adsorption rate was measured by analyzing the concentration of a supernatant.

TABLE 7

| Carbamazepine-bentonite ratio | Drug adsorption rate (%) |
|---|---|
| 1:1 | 46.5 ± 1.6 |
| 1:2 | 52.0 ± 0.9 |
| 1:3 | 63.7 ± 0.5 |
| 1:5 | 81.2 ± 0.4 |
| 1:10 | 93.7 ± 0.1 |

Figure 19:
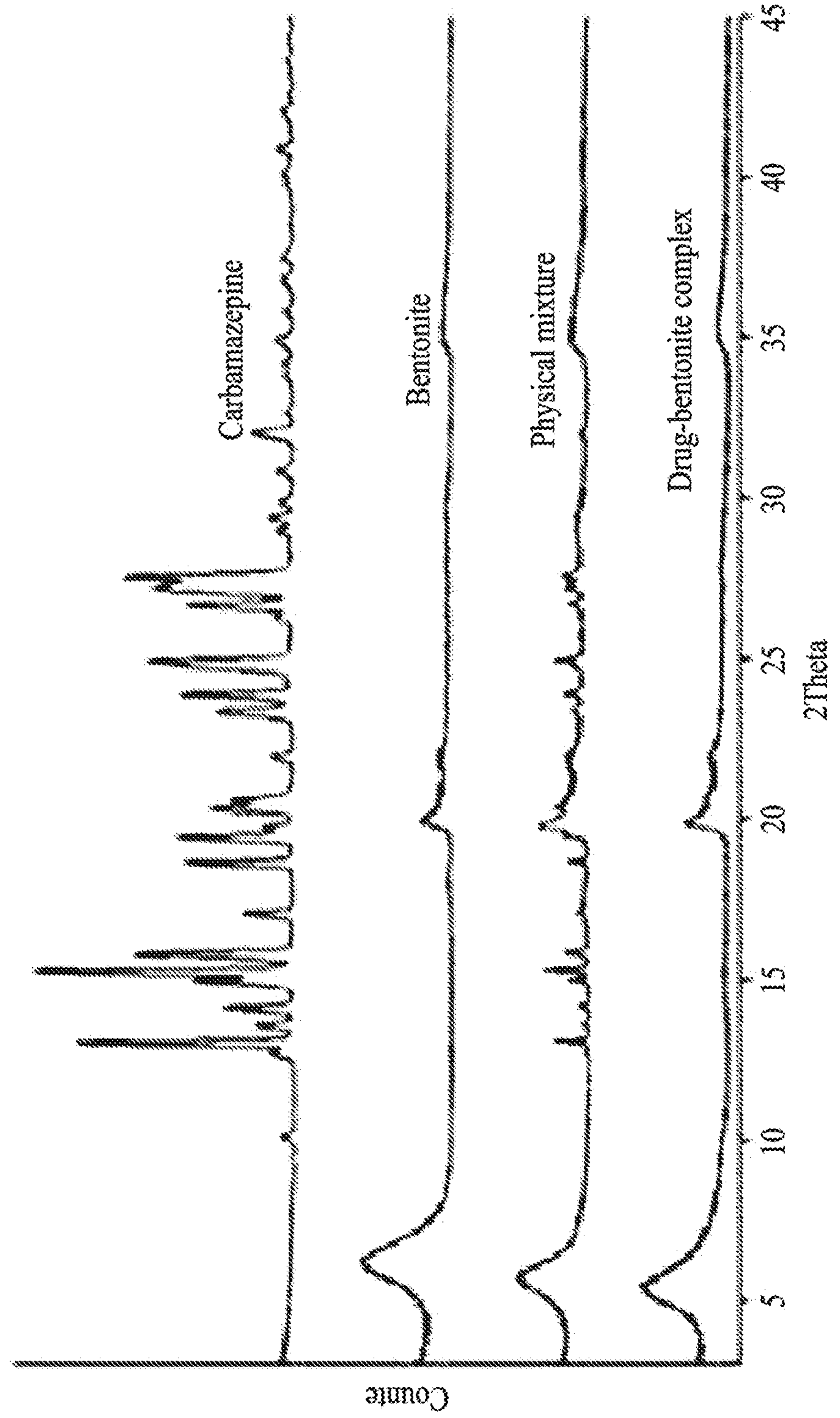
FIG. 19 is a diagram illustrating an XRD pattern of a carbamazepine-bentonite complex according to an example embodiment.

As a result, the drug adsorption rate was shown when the weight ratio of carbamazepine and bentonite was 1:5, and a carbamazepine-bentonite complex was prepared at the corresponding ratio, and physical properties and drug delivery performance were evaluated. The crystallographic characteristics of the carbamazepine-bentonite complex were analyzed using X-ray diffraction analysis (XRD) (a D8 ADVANCE model from Brucker Co., Ltd. was used, a copper cathode was used as an X-ray source, a wavelength of the X-ray was 1.5418 Δ, and the analysis was performed in a 2θ range of 3 to 40). It was found that the drug-specific peaks appearing in physical mixtures with conventional drugs were not shown in the complex, so that it was confirmed that carbamazepine was encapsulated in bentonite in an amorphous state (see FIG. 19).

Figure 20:
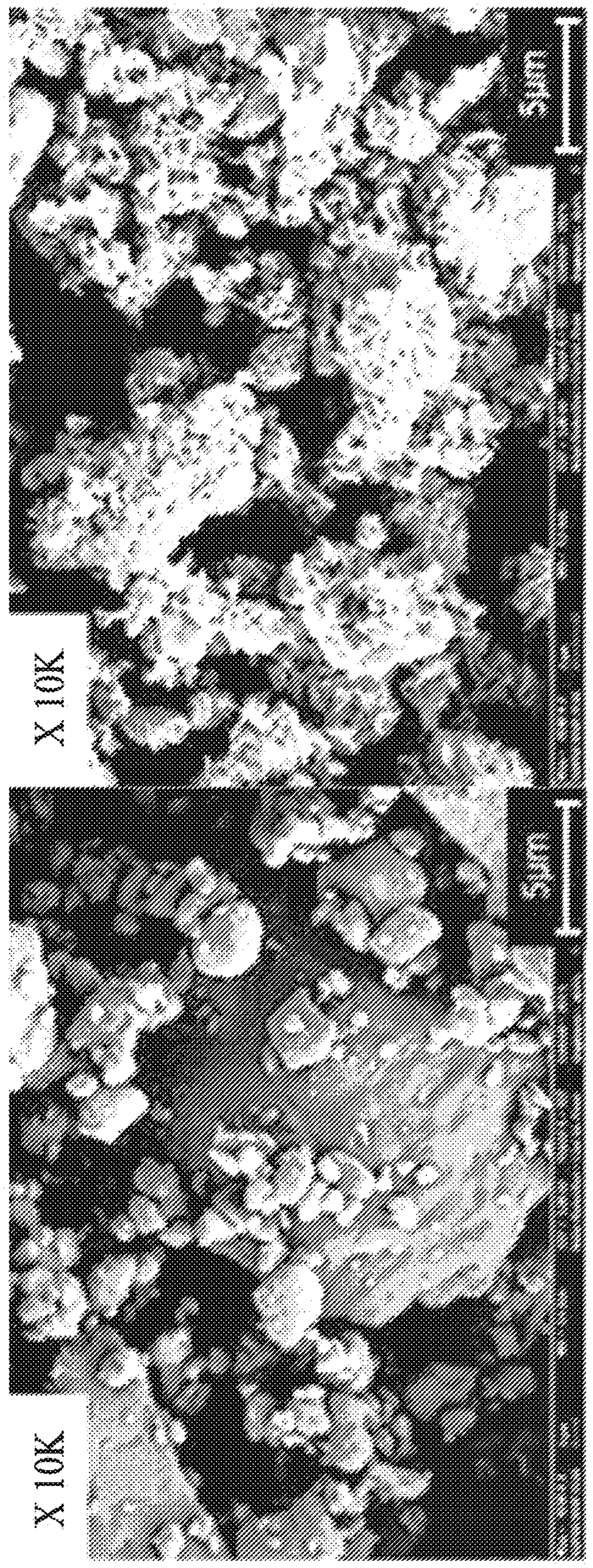
FIG. 20 is a diagram illustrating SEM images of carbamazepine powder (left) and a carbamazepine-bentonite complex (right) according to an example embodiment.

In addition, as a result of observing the form of the complex with the drug using an electron microscope (SEM), in the case of an existing carbamazepine drug, drug particles having sizes of 1 μm or more were observed, but in the carbamazepine-bentonite complex, these particles disappeared and only an irregular layered structure unique to bentonite was observed. This means that the drug does not exist separately after the drug-bentonite adsorption process but is adsorbed in an amorphous form in the layered structure (see FIG. 20).

Figure 21:
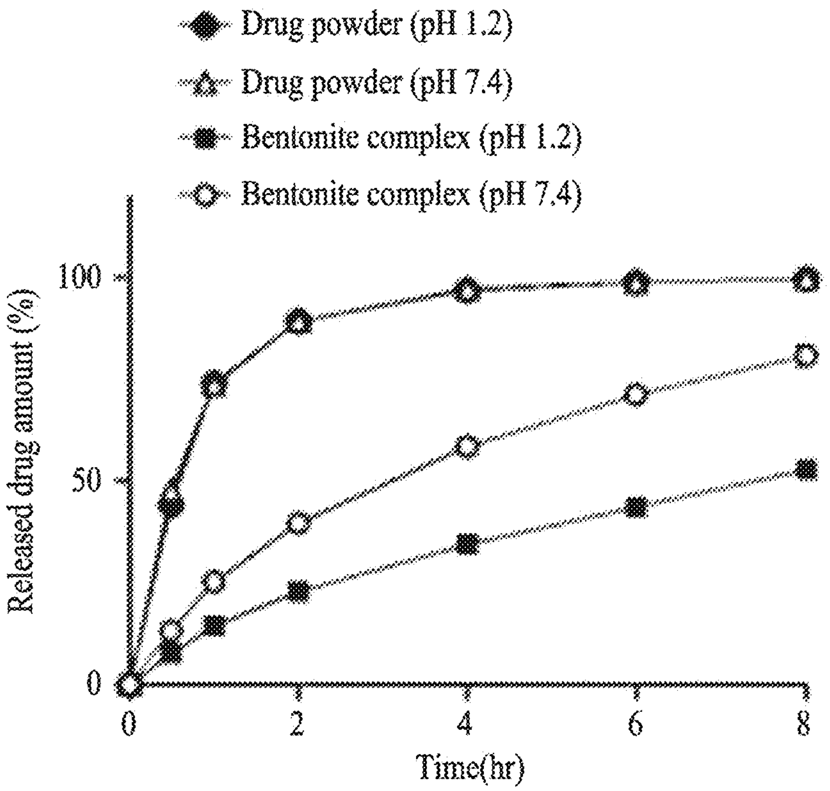
FIG. 21 is a diagram illustrating drug release patterns of a carbamazepine-bentonite complex according to a pH condition according to an example embodiment.

Next, as a result of the drug release test, most of carbamazepine powder was released within 2 hours regardless of pH, whereas the release rate was significantly lower in the case of the carbamazepine-bentonite complex (see FIG. 21). In addition, a pattern released at a constant rate at all pHs was shown, and since the release rate of carbamazepine is higher at high pH, it may be inferred that the drug may be easily released from the lower digestive tract.

As described above, although the example embodiments have been described by the restricted drawings, various modifications and variations may be applied on the basis of the example embodiments by those skilled in the art. For example, even if the described techniques are performed in a different order from the described method, and/or components such as a system, a structure, a device, a circuit, and the like described above are coupled or combined in a different form from the described method, or replaced or substituted by other components or equivalents, an appropriate result may be achieved.

Therefore, other implementations, other example embodiments, and equivalents to the appended claims fall within the scope of the claims to be described below.

What is claimed is:

1. A drug-clay mineral complex, wherein the complex contains a phospholipid, and wherein:

the drug in the drug-clay mineral complex is present in an amorphous state in a layered structure of the clay mineral, said drug has an amine group and is at least one selected from the group consisting of quetiapine, ciprofloxacin, docetaxel, camptothecin, carbamazepine, and said phospholipid is phosphatidylcholine, and the clay mineral is bentonite.

2. The drug-clay mineral complex of claim 1, wherein 2 to 30 wt % of the phospholipid and 1 to 50 wt % of the drug are included.

3. The drug-clay mineral complex of claim 1, wherein a maximum drug release rate in a release solution at pH 7.4 is increased by 1.5 times greater than a drug-clay mineral complex having the same composition except that the phospholipids is not included.

4. The drug-clay mineral complex of claim 1, wherein the maximum drug release rate in the release solution at pH 7.4 is 80% or more of the drug content.

5. An oral administration composition comprising the drug-clay mineral complex according to claim 1.

6. A method of preparing a drug-clay mineral complex comprising:

preparing a phospholipid-clay mineral complex by mixing a phospholipid aqueous solution prepared by dissolving a phospholipid in an organic solvent and a hydrophilic solvent and a clay mineral suspension;

preparing an aqueous drug solution by dissolving a drug compound having an amine group in a hydrophilic solvent; and mixing the aqueous drug solution and a suspension of the phospholipid-clay mineral complex, wherein:

the drug in the drug-clay mineral complex has an amine group and is at least one selected from the group consisting of quetiapine, ciprofloxacin, docetaxel, camptothecin, carbamazepine, and said phospholipid is phosphatidylcholine, and the clay mineral is bentonite.

7. The method of claim 6, wherein the organic solvent is at least one selected from the group consisting of methanol, ethanol, propanol, acetone, acetonitrile, butanediol, diethanolamine, formamide, dimethylformamide, dimethylsulfoxide, dimethylacetamide, glycerol, tetrahydrofuran, and propylene glycol.

8. The method of claim 6, wherein the hydrophilic solvent is an acidic aqueous solution having a pH of 5 or less.

9. The method of claim 8, wherein the acidic aqueous solution contains at least one selected from the group consisting of hydrochloric acid, phosphoric acid, sulfuric acid, acetic acid, and formic acid.

* * * * *